United States Patent [19]
Skladnev et al.

[11] Patent Number: 6,026,323
[45] Date of Patent: Feb. 15, 2000

[54] TISSUE DIAGNOSTIC SYSTEM

[75] Inventors: Victor Skladnev, Vauchse; Richard Thompson, Killarnegheiglh, both of Australia; Irwin Wunderman, Mountain View, Calif.; David Bull, Epping, Australia; Neil Edwards, Artarmon, Australia; Stephen Rowe, Blaxland, Australia; Gregory Smart, Randwick, Australia; Megan Smith, Camperdown, Australia

[73] Assignee: Polartechnics Limited, Sydney, Australia

[21] Appl. No.: 08/934,152

[22] Filed: Sep. 23, 1997

Related U.S. Application Data

[60] Provisional application No. 60/041,116, Mar. 20, 1997.

[51] Int. Cl.[7] .................................................. A61B 5/05
[52] U.S. Cl. .................................................. 600/547
[58] Field of Search ........................ 600/426, 407, 600/547, 591, 548; 607/901

[56] References Cited

U.S. PATENT DOCUMENTS

| | | | |
|---|---|---|---|
| 4,184,486 | 1/1980 | Papa | 128/642 |
| 4,458,694 | 7/1984 | Sollish et al. | 128/734 |
| 5,143,079 | 9/1992 | Frei et al. | 128/734 |
| 5,233,982 | 8/1993 | Kohl | 607/5 |
| 5,361,762 | 11/1994 | Gunter | 128/653.1 |
| 5,409,011 | 4/1995 | Alexeev et al. | 128/734 |
| 5,427,113 | 6/1995 | Hiroshi et al. | 128/734 |
| 5,630,426 | 5/1997 | Eggers et al. | 128/734 |
| 5,697,369 | 12/1997 | Long, Jr. | 128/653.1 |
| 5,713,364 | 2/1998 | DeBaryshe et al. | 128/664 |
| 5,792,053 | 8/1998 | Skladnev et al. | 600/407 |
| 5,800,350 | 9/1998 | Coppleson et al. | 600/372 |

*Primary Examiner*—Francis J. Jaworski
*Assistant Examiner*—Ali M. Imam
*Attorney, Agent, or Firm*—Gottlieb, Rackman & Reisman, P.C.

[57] ABSTRACT

A probe type instrument to characterize tissue type that combines optical and electrical tests in a single device capable of providing data of both types almost simultaneously from very small, e.g. 3–10 mm diameter, areas of tissue surface. Key to this approach is an instrument capable of making almost simultaneous electrical and optical measurements on the same small areas of tissue, before being moved to scan adjacent tissue areas. In the preferred operation of the system fourteen measurement cycles are performed per second and each measurement involves a complex sequence of events, including (1) three optical and fifteen electrical tissue stimulations with subsequent detection, filtering and digitization of the tissue response; (2) extraction of specific parameters from the optical and electrical signals; (3) checking for errors, and subsequent classification of the extracted parameters into various tissue type categories; and (4) feedback to the system operator. Thus on the order of 15,000 measurements are made per one minute patient examination.

27 Claims, 12 Drawing Sheets

LED1 = GREEN
LED2 = RED
LED3 = BLUE
LED4 = BLUE
LED5 = BLUE

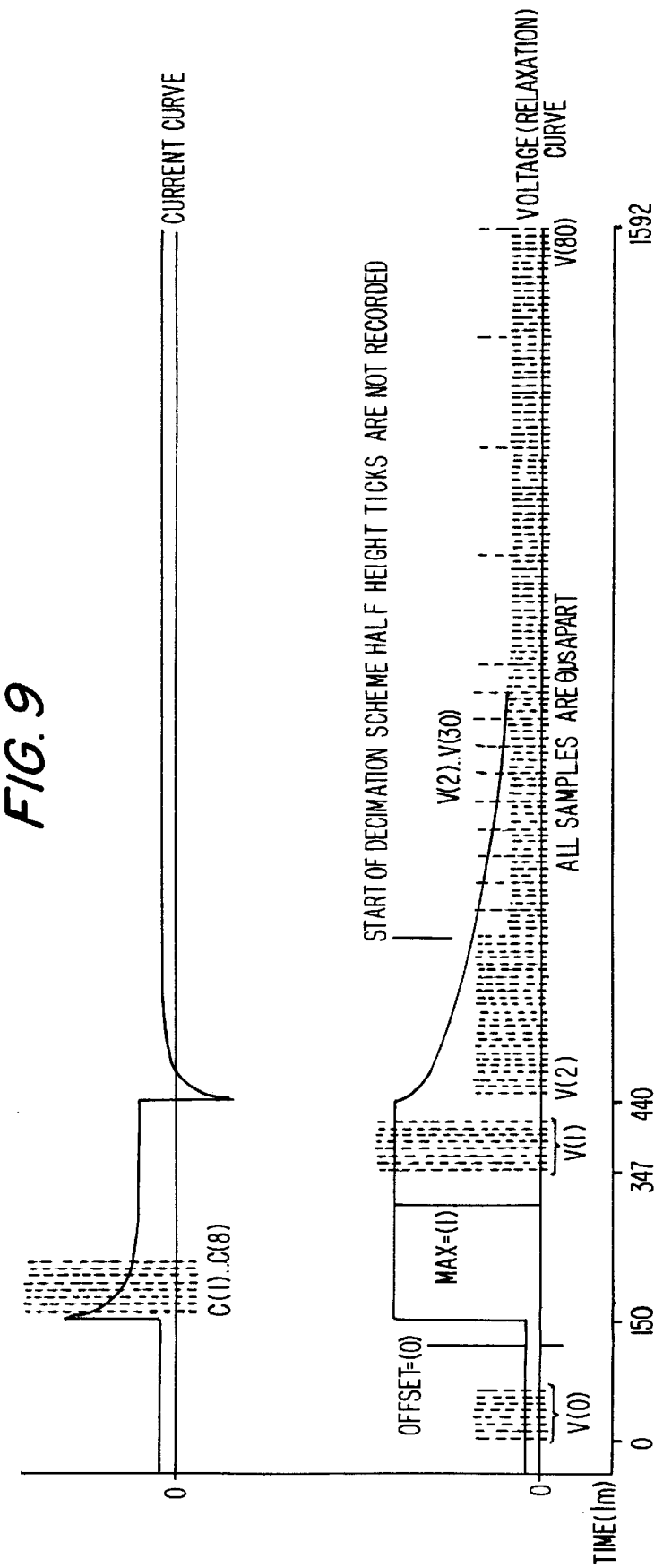

TISSUE DIAGNOSTIC SYSTEM

This application claims benefits of Provisional Appl. No. 60/041,116 filed Mar. 20, 1997.

FIELD OF THE INVENTION

This invention relates to systems that identify tissue type in a patient by the use of combinations of optical and electrical measurements on tissue surfaces. The measurements are compared with data gathered from prior patient studies, and the patient's tissue is then categorized.

BACKGROUND OF THE INVENTION

The identification of tissue type based upon responses to incident light and/or electrical stimulation is well known. This has led to diagnostic techniques and apparatus for identifying tissue types such as cancerous or pre-cancerous. Existing techniques for identifying cancers run the gamut from microscopic examination of tissue smears by trained cell pathologists, to the study of the fluorescence, electrical and other physical properties of tissues. Much research has been devoted to the identification and comparison of optical and electrical characteristics of healthy and damaged tissue in the hope that it could lead to new diagnostic techniques. The research is driven by the fact that none of the present methods for the detection of cervical cancers are sufficiently accurate, and the risks of incorrect diagnosis are severe. Many cancerous conditions, especially cervical cancers, are treatable by removal of the involved area if caught in time, but become deadly if not.

The Papanicolaou ("Pap") smear has been the method of choice for cervical screening for over 50 years. The sensitivity limitations of the Pap smear have been well documented, and include an overall false negative rate variously reported as between 20–40%, and between 6–55%. False negative rates for pre-cancerous lesions have been assessed as 28%, and between 20–50%. In addition, the estimated specificity for the test has been profoundly affected by the widespread introduction in the USA of the Bethesda cytology classification system. The system, introduced in 1989 and revised in 1991, introduced a new cytologic category, Atypical Squamous Cells of Undetermined Significance (ASCUS). It has been noted that "ASCUS is not a morphologic entity, but rather an 'I don't know' category"; "ASCCP Practice Guideline: Management guidelines for follow-up of Atypical Squamous Cells of Undetermined Significance (ASCUS)", *The Colposcopist* 1996: XXVII(1), 1–12. Other equivalent cytological categories including morphologic changes bordering on mild dyskaryosis, atypical cells, minor atypia and minimal atypia also represent a high false positive rate if all women with screening results in these categories are referred for diagnostic examination.

Most research has focused on isolated techniques, either optical (reflecting or scattering light or infra-red radiation from tissue), or electrical (studying the conductivity of tissue at different depths below the surface), or otherwise responding to such things as magnetic fields or pressure. Fricke and Morse, in 1926, conducted a study involving the electrical measurement of breast tumors; Fricke H and Morse S, "The electric capacity of tumors of the breast". *J Cancer Res* 1926: 10, 340–76. This was followed in 1949 with a study of electrical parameters derived from measurements of cervical tissue by Langman and Burr who found "significant differences in cancerous and non-cancerous tissue". Langman L J and Burr H S, "A technique to aid in the detection of malignancy of the female genital tract", *Am J. Obstet Gynecol* 1949: 57, 274–81. Researchers have measured various physical properties of tissue samples for many years, many having concentrated on bulk properties of tissue rather than concentrating on the epithelial layers. Very few groups have been successful in a transition to in vivo studies. Some examples of work which specifically focused on examination of epithelial tissue are as follows:

The impedance of single layers of cultured cells grown across electrodes has been used to assess their growth and physiological activity under various circumstances. Hyun, C. H., et al., "Morphological Factors Influencing Transepithelial Conductance in a Rabbit Model of Ileitis," *Gastroenterology*, 1995; 109:13–23. Epithelium has been removed from the body, prepared and placed in experimental apparatus for detailed measurement of its electrical properties. Kottra, G. et al., "Rapid Determination of Intraepithelial Resistance Barriers by Alternating Current Spectroscopy," *Pflugers Archiv: European Journal of Physiology*, 1984; 402:409–420. Electrical impedance tomography has been used to develop a technique for imaging deeper structures in the body by mapping impedance measurements across the surface of the skin. This technique tries to deliberately eliminate the effect of the surface epithelium. Webster, J. G., *Electrical Impedance Tomoaraphy*, Bristol & New York: IOC Publishing, 1990. The use of the scattering of light to characterize tissue is known. Bigio, I. J. et al., "Optical Diagnostics Based on Elastic Scattering: An Update of Clinical Demonstrations with the Optical Biopsy System", *SPIE* 2324:46–54, 1994. Representative patents are U.S. Pat. No. 4,407,300, "Potentiometric diagnosis of cancer in vivo"; U.S. Pat. No. 5,353,802, "Device for measurement of electrical impedance of organic and biological materials"; U.S. Pat. No. 5,439,000, "Method of diagnosing tissue with guide-wire"; and U.S. Pat. No. 5,560,357, "D.C. epidermal biopotential sensing electrode assembly and apparatus for use therewith". Representative publications are: Avis, N. J. et al. (post 1995) "In-vitro multifrequency electrical impedance measurements and modeling of the cervix in late pregnancy"; Marino, A. A. et al.(Undated Abstract), "On the relationship between surface electrical potentials and cancer"; Melczer (1977), "Electrical potentials in epithelial neoplasms", British Jour. of Dermatology 96, 572; and Thornton (1991), "Relaxation distribution function of intracellular dielectric zones as an indicator of tumorous transition of living cells", IMA Jour. of Math. Applied in Med. & Bio. 8, pp. 95–106.

U.S. Pat. Nos. 5,042,494 and 5,348,018 are typical of those that concern the examination of tissue absorption, fluorescence and autofluorescence applied to melanomas and other tissue types. These techniques are further discussed in Van Gemert, M. J. C. et al., "Skin Optics". *IEEE Transactions on Biomedical Engineering* 36(12):1146–1154, 1989; and Tuchin, V. V., (ed.), *Selected Papers on Tissue Optics—Applications in Medical Diagnostics and Therapy*, SPIE Milestone Series, Volume MS 102. Representative patents are: U.S. Pat. No. 4,213,462, "Optical assembly for detecting an abnormality of an organ or tissue and method"; U.S. Pat. No. 4,930,516, "Method for detecting cancerous tissue using visible native luminescence"; U.S. Pat. No. 5,036,853, "Use of light conveyed by fiber optics to locate tumors. Physiological probe"; U.S. Pat. No. 5,042,494, "Method and apparatus for detecting cancerous tissue using luminescence excitation spectra"; U.S. Pat. No. 5,131,398, "Method and apparatus for distinguishing cancerous tissue from benign tumor tissue, benign tissue or normal tissue using native fluorescence"; U.S. Pat. No.

5,179,938, "Apparatus for endoscopic examination of body cavity using chemiluminescent light source"; U.S. Pat. No. 5,348,018, "Use of fluorescence or luminescence. Method for determining if tissue is malignant as opposed to non-malignant using time-resolved fluorescence spectroscopy"; and U.S. Pat. No. 5,413,108, "Method and apparatus for mapping a tissue sample for and distinguishing different regions thereof based on luminescence measurements of cancer-indicative native fluorophor". Representative publications are: Bigio et al. "Non-invasive identification of bladder cancer with sub-surface backscattered light." SPIE Symp. on Biomed. Optics, Jan. 2–28, 1994; Bigio, et al. "Optical diagnostics based on elastic scattering: recent clinical demonstrations with the Los Alamos Optical Biopsy System" SPIE Vol. 2081 Optical Biopsy (1993); Coppleson, M., et al. "An electronic approach to the detection of pre-cancer and cancer of the uterine cervix: a preliminary evaluation of Polarprobe" Int'l Gynecol Cancer 1994, 4, 79–83; Coppelson et al. 1991 Prototype Cervix Probe. Abstract in Int. J. Gynecol. Obstet. XIII World Congress Of Gynecology and Obstetrics; and Wagnieres, G. et al. (1990) "Photodetection of early cancer by laser induced fluorescence of tumor-selective dye: apparatus design and realization". SPIE Vol. 1203 Photodynamic Therapy Mechanisms II.

The background technology of the present invention has been described in Wunderman et al., "A precancer detection instrument," J. Gynecol Tech. 1995: 1(2), 105–9 and Thompson R L et al., "A non-invasive probe for cervical cancer detection", Proceedings IE Aust. Electrical Engineering Congress 1994.

BRIEF DESCRIPTION OF THE INVENTION

The present invention is a novel system designed for the detection of cervical precancer and cancer. The system is a portable optoelectronic instrument capable of giving the physician operator an instantaneous result without requiring tissue sampling for cytologic analysis. As the operator scans the cervix with the probe of the system, the device interrogates the cervical tissue using a combination of low level electrical impulses and light pulses at various frequencies. The measured response, or tissue signature, is compared algorithmically in real time to that stored in a databank of cervical tissue types. If a match is found, the result is classified into one of three categories: normal, low grade squamous intraepithelial lesion (LSIL), or high grade squamous intraepithelial lesion/invasive cancer (HSIL/IC). With the aid of digital signal processing and discriminant analysis statistical techniques, a large number of parameters can be measured and processed in real time.

The present invention provides an instrument preferably capable of providing both optical and electrical data almost simultaneously from very small sections of tissue surface. Although there is no evidence that the optical properties of tissue are affected by electrical stimulation, or vice-versa, it has been unexpectedly determined that properly combining the data from both types of tests on the same small region of tissue, on the order of a few millimeters diameter, e.g. 3–10 mm, provides a statistically significant increase in the predictability of success of tissue diagnosis. Key to this approach is an instrument capable of making almost simultaneous electrical and optical measurements on the same small section of tissue, before being moved to scan an adjacent tissue areas. An instrument that makes this type of examination feasible has been described in our EPO publication 0 050 694 A1, May 3, 1995, whose disclosure is incorporated by reference. The complete instrument includes a probe and an accompanying console unit. The present disclosure concerns improvements in the console electronics and its controls over the probe measurements to be taken. Other improved probes, sometimes referred to as "hybrid probes" in our earlier work, are disclosed in our copending U.S. application Ser. No. 08/818,912 entitled, "Hybrid Probe For Tissue Type Recognition", 08/818,930 entitled, "Apparatus For Tissue Type Recognition Within a Body Canal", 08/823,660 entitled "Sheathed Probes For Tissue Type Recognition", 08/818,912 entitled "Hybrid Probe For Tissue Type Recognition", 08/818,921 "Sheath For an Endocervical Probe", and 08/818,910 entitled "Integral Sheathing Apparatus For Tissue Recognition Probes", all filed on Mar. 17, 1997 the disclosures of which are also incorporated herein by reference.

The present invention concerns the sequencing of the optical and electrical tests on tissue selected by contact with the probe. Selection by contact refers to the ability of the probe to determine the properties of a particular small tissue segment that is contacted by the probe tip and possibly a small area of adjacent tissue. In the case of electrical properties, the currents caused to flow by the probe do not necessarily flow as surface currents, but may penetrate more deeply into the surface and thus more than superficial cells may also be responsible for the probe test results and are considered to be selected by contact. The invention resides in the relationship between the optical and electrical measurements and the statistical analysis of parameters defined as linear combinations of both types of data.

In the preferred operation of the system, fourteen measurement cycles are performed per second and each measurement involves a complex sequence of events, including (1) optical and electrical tissue stimulation and detection, and filtering and digitization of the tissue responses;

(2) extraction of 21 specific parameters from the optical and electrical signals in each overall cycle;

(3) checking for errors, and subsequent classification based on the derived parameters into various tissue type categories; and (4) feedback to the system operator.

A complete scan of the cervix typically takes between one and two minutes. Therefore, during a one minute scan the total number of data parameters processed is on the order of 15,000.

BRIEF DESCRIPTION OF THE DRAWINGS

FIG. 9 is a timing diagram for a single electrical measurement voltage relaxation curve indicating the points in time at which measurements of the voltage amplitude are made.

DETAILED DESCRIPTION OF PREFERRED EMBODIMENTS

General Introduction:

The present invention provides a method and apparatus for tissue type recognition which is useable at a variety of locations within or about a living being and which can quickly produce an objective identification of the tissue types, including the presence of pre-cancerous and cancerous activity. The probes of this invention are designed to distinguish between tissue types when held directly against tissues in the body that are accessible without damage to the tissue. This is primarily the external covering and lining tissues that are collectively termed "epithelial tissues."

General Description of Epithelial Tissues Subject to Examination:

Epithelial membranes form the covering and lining of the major organs of the body. These epithelial layers are highly structured arrangements of cells. Under them is connective tissue which is more loosely structured and which includes other components such as blood and lymphatic vessels. In turn, under these are other organ structures.

The epithelial layer functions primarily to protect the underlying connective tissue from wear and damage. This is best exemplified by the skin but can also be seen in the lining of the intestinal, respiratory and urogenital tracts. Epithelial tissues can also have secretory and absorptive functions; for example, the lining of the respiratory tract secretes a mucous to prevent the tissue drying out, and the small intestine has the specialized function of absorbing nutrients from digested food.

The covering or lining of many organs is easily reached from outside without puncture or tissue damage. Access can be either directly, such as to the skin, oral mucosa and the eye, or indirectly via an instrument such as a speculum to the vagina and cervix or an endoscope to the sinuses, trachea, bronchi, oesophagus, stomach, intestine, uterus and bladder.

Figure 1:
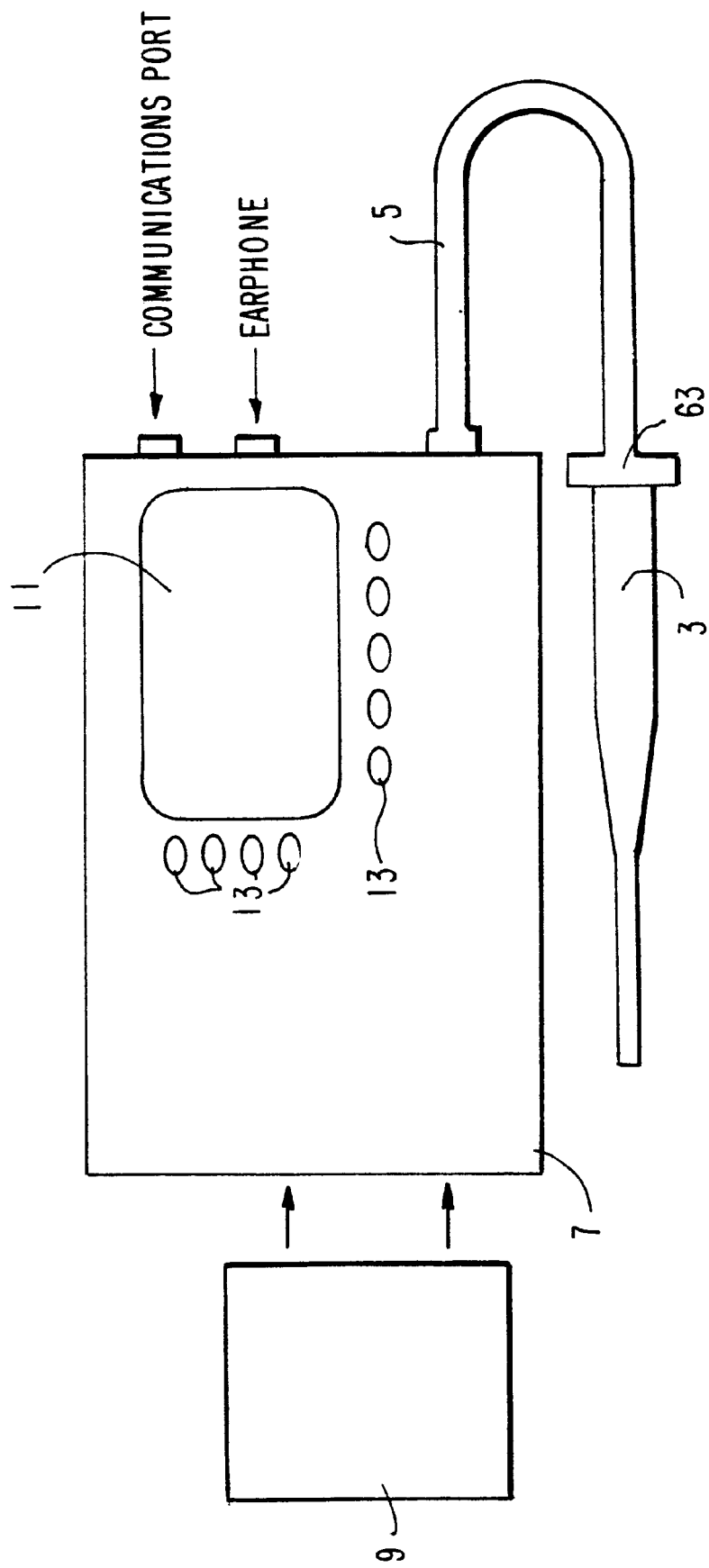
FIG. 1 is a schematic view of the apparatus of the present invention.

General Description of the Apparatus:

The apparatus of the present invention is shown in FIG. 1. It comprises a pen-shaped probe 3, connected via a flexible probe cable 5, a probe console 7 approximately the size and shape of a laptop computer, and a removable mains pack or battery pack 9. The probe 3 is a hand held device about 27 cm in length at the proximal end of which (the handle) the probe diameter is approximately 2.5 cm. The device tapers towards its tip and the distal end is approximately 5 mm in diameter. The probe is soak-sterilizable in 2% glutaraldehyde solution. The connection of a serial cable is possible for purposes of data transfer and storage. An earphone may be used to give an audible diagnosis. Diagnostic information is presented on a Liquid Crystal Display (LCD) 11. A simple keyboard 13 wraps around the LCD.

Figure 2:
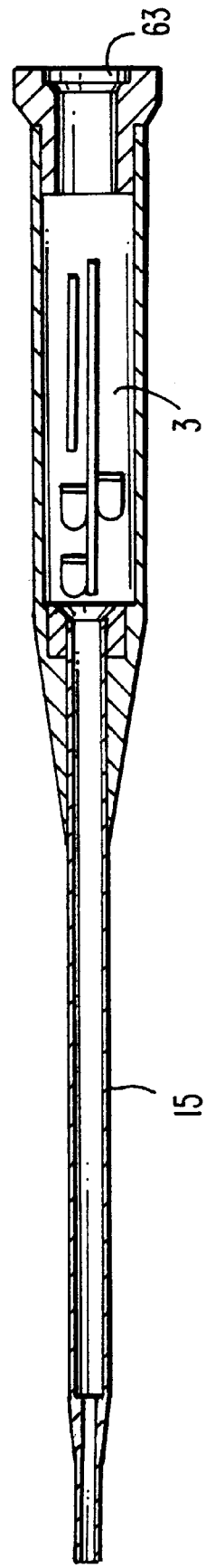
FIG. 2 is a cross section view of the probe of the present invention.
Figure 3:
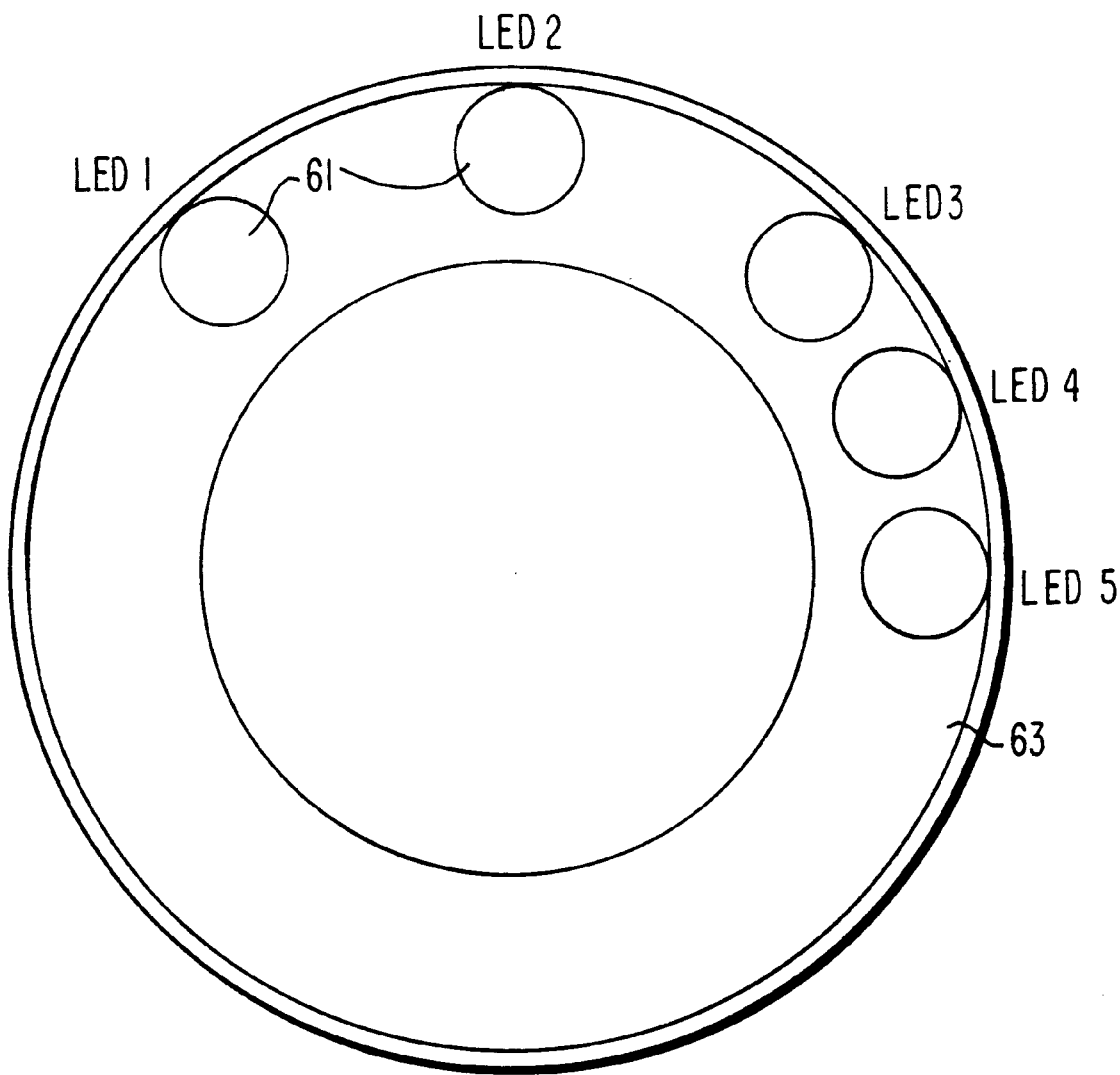
FIG. 3 is a cross section drawing of the rear of the probe of the present invention.
Figure 5:
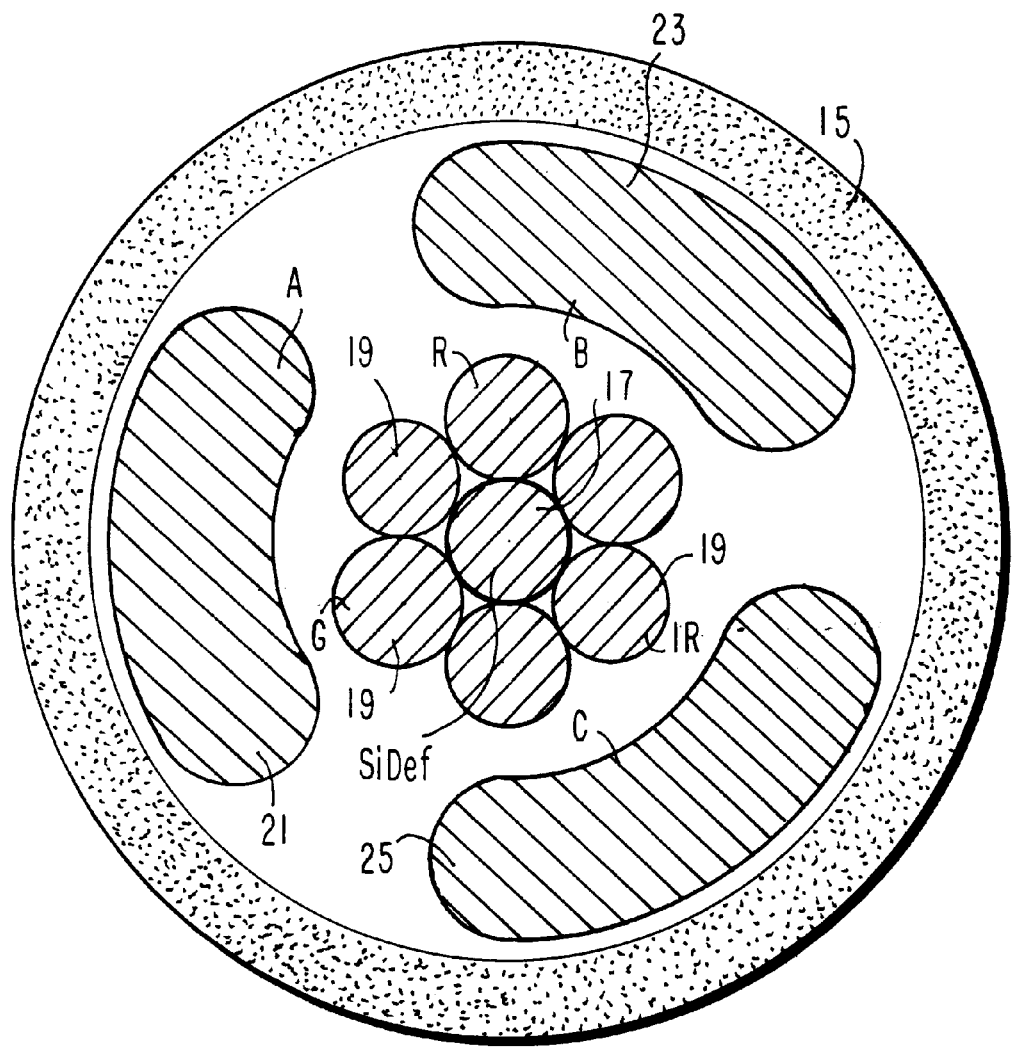
FIG. 5 is a cross section drawing of the tip of the probe of the present invention.

The probe is shown in longitudinal cross section in FIG. 2, the rear of the probe is shown in cross section in FIG. 3, and the probe tip is shown in cross section in FIG. 5. The probe has located within an external tube 15 a central optical fiber 17 which conducts electromagnetic radiation to a photo-detector diode in the handle and which is positioned in the center of a bundle of optical fibers 19 extending from LEDs in the handle to the tip of the probe. Three gold electrodes 21, 23, and 25 are positioned adjacent and abutting against the internal surface of the external tube 15. In one embodiment, the probe cable 5 consists of 16 individual coaxial conductors with a single overall braided shield, enclosed in a medically rated silicone outer jacket. Both ends of the cable have round plastic 16 pin male connectors. In another embodiment, only 4 conductors are used and digital signals are employed.

The electrodes 21, 23, and 25 and optical fibers 17 and 19 come into direct contact with the cervix tissue for stimulation and detection of the tissue characteristics. The probe tip is polished and smoothed and has contoured edges. An epoxy resin electrically insulates and seals the tip section.

The hand-held probe, which comes into contact with the cervix, continuously interrogates the cervical tissue by repetitively pulsing it with low levels of optical and electrical energy. Real-time interpretation of the cervix tissue response is achieved by a statistical classification algorithm in software resident in the probe console. The measured tissue response is then compared to a catalogue of tissue signatures and the operator informed of the result. Tissue will be classified as normal, low grade abnormality, or high grade abnormality/invasive cancer. An operator error may also be flagged.

Figure 4:
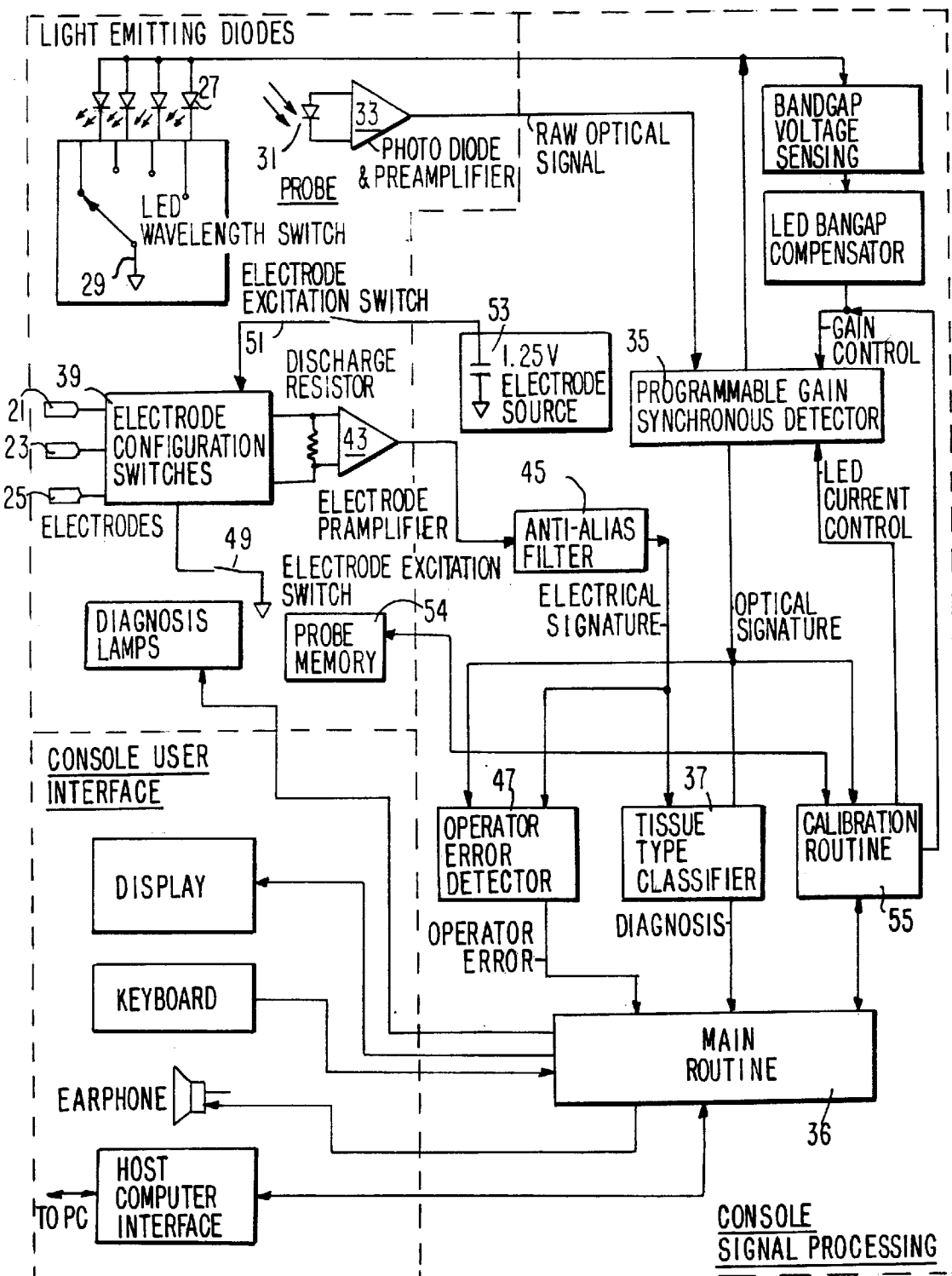
FIG. 4 is a system block diagram of the components of the system of the present invention.

A block diagram of the relationship between the components of the probe system is given in FIG. 4, which is divided into sections representing the probe, the console user interface, and the console signal processing section. All of the functional blocks that appear in the probe section of the system block diagram are implemented within the probe handle.

As shown in FIGS. 4–5, light emitting diodes (LEDs) 27 mounted in the handle of the probe are used as the light source to measure the level of backscattered light returning from the cervix. In another embodiment, the LEDs can be positioned at the tip of the probe without the use of fibers to conduct the light to the tip.

The LEDs are excited in turn by selecting the appropriate device via the LED wavelength switch 29. Light from the selected LED is carried by optical fibers 19 to the tissue under examination. The LEDs operate at three distinct wavelengths, red and green in the visible spectrum and infrared, to provide the light to the fibers 19. The resultant backscattered light is directed via optical fiber 17 to a photodiode 31 that produces a photocurrent, which is locally converted into a voltage by the preamplifier 33. The photodiode 31 can also be positioned, in an alternative embodiment, at the tip of the probe without the use of fibers to conduct the light from the tip to the photodiode.

The resulting raw optical signal is received by a programmable gain synchronous detector 35, which under the control of a microprocessor 36 labeled "main routine" in the figure provides output to the tissue type classifier 37 in which diagnosis is accomplished together with information derived from the concurrent electrical testing information.

The electrodes 21, 23, and 25 interface with electrode configuration switches 39, electrode excitation switches 49 and 51 and an electrode preamplifier 43. This provides signals via an anti-aliasing filter 45 to the tissue type classifier 37 and operator error detector 47 to the microprocessor 36. The electrodes can thus be selected to be anodes, cathodes or high impedance (no connection) through the switch 39, which is controlled by the microprocessor 36. To improve the signal-to-noise ratio the electrode preamplifier 43 is also located in the probe handle. The electrode preamplifier is connected in a differential configuration to reduce the effects of common mode noise sources.

A voltage of 1.25 volts is applied to the electrodes to charge the cervical tissue. After a short period of time (250 $\mu$s) the voltage source is disconnected by the two electrode excitation switches 49, 51. The electrode supply (electrode source) 53 provides the voltage for charging the cervical tissue. This supply has suitable over-voltage and over-current protection for the safety of the patient.

The signal processing section shown in FIG. 4 comprises the analog signal conditioning and the tissue classifier. The analog signal conditioning is responsible for the conversion of the probe signals into signals suitable to interface to the microprocessor's analog-to-digital and digital-to-analog convertors. The tissue classifier resides in software running on the microprocessor.

Probe dependent calibration data is stored in a nonvolatile probe memory 54, which interfaces with a calibration routine 55 stored in the microprocessor 36. This enables the system console to customize its response to a new probe. Encoded operational coefficients in the probe memory 54 refer to embedded particular operational characteristics and instructions that are read by the console to achieve a calibrated response from the probe. The importance of probe calibration is so the algorithm for tissue classification need not be hardware specific. Since this calibration data is stored within the probe, the console and probe do not have to be matched. Having probe specific information stored within the probe, as opposed to the console, has the advantage of an easier validation and makes it less complicated to upgrade the system via the probe than would be the case if it was required to upgrade the console. The console reads these characteristics from the probe and adjusts its probe driving and probe sensing circuit to make all probes behave the same or at least similarly. In addition to probe calibration data, probe storage may include algorithm coefficients or other modular algorithm components or firmware units. Once the probe's optical and electrical signatures have been sampled by an analog-to-digital convertor, processing of signals is performed in the digital domain by the microprocessor. The microprocessor is controlled by a "main routine." The main routine is responsible for the reporting of a diagnosis or operator error to the user. It is also responsible for requesting the periodic calibration of the probe.

The Individual Tests: Electrical

The electrical analysis is particularly suited to epithelial tissues. An electrical contact is formed between the electrodes and tissue by the presence of an electrolyte. This may be a naturally occurring mucus covering the tissue or an artificially applied conductive fluid or gel. The electrodes are held against the tissue so that only a thin layer of electrolyte remains between the two. The impedance of this thin layer is relatively low through to the tissue but relatively high between the electrodes so electric current is directed through the epithelium. The epithelium presents a layer of moderate impedance and beyond it is connective tissue of substantially lower impedance. The electrical measurement is thus dominated by the properties of the epithelial covering.

The impedance of the epithelial layer at low frequency depends on its particular characteristics. Various mechanisms have been proposed to account for differences between tissue impedances. For an epithelial layer, this includes its thickness, the tightness of the intercellular junctions, the strength of the basement membrane, the cellular arrangement, the extracellular space (between the cells) and the composition of the extracellular fluid. At high frequency, the cell membranes capacitively couple to the intracellular spaces and so the internal composition of the cells also becomes important.

The Individual Tests: Optical

Because there is no direct path, the light which reaches the optical detector from the source must first scatter through the tissue under the tip of the probe. The path of scatter depends on the wavelength and affects the intensity of the light. It will be influenced by many characteristics of the epithelium and underlying connective tissue including the cellular arrangement, the size and shape of cell components such as the nucleus and mitochondria, the vascularization and the fluid levels in the tissue. Along this path some of the light will be absorbed by various cell components such as chromatin, hemoglobin and the opacity of the tissue. The amount of absorption is dependent on the wavelength of light. Differences between the absorption at different wavelengths can be very informative in differentiating between tissue types. During each measurement cycle, the LEDs are activated in sequence. The detector photodiode is used for the detection and measurement of backscattered light across the spectral range encompassed by the three LEDs. Significant background noise is encountered due to ambient light and examination lighting, and the signal to noise ratio is boosted by means of a variable gain amplifier system. Ambient light compensation is achieved by performing a set of ambient measurements immediately pre- and post-LED activation. The backscattered optical signal is recovered and then filtered and digitized.

Typical Measurement Cycle

The electrical measurements are stimulated by the delivery of 1.25 volt electrical pulses of 250 $\mu$s duration. Following removal of the applied electrical potential, the residual charge dissipates within the tissue with a decay constant dependent on tissue capacitance, the electrode/tissue interface and electronic and ionic conductance. This "relaxation curve" is characteristic of the underlying tissue type (FIG. 9). The shape of the electrical relaxation curve is also highly dependent on hardware-specific features including the electrode material composition, surface composition and position. The measured tissue response is filtered, digitized at 9 $\mu$s intervals, and thereafter processed in the probe console.

It is preferable in some probe configurations to use only two electrodes in which case the electrical pulses are applied across these with periodic reversal of polarity to minimize electrochemical degradation. Because the three electrode configuration is the more general form of the device, the typical measurement cycle is described below with reference to that form. Where three electrodes are employed, the electrical pulses are delivered across varying combinations of these electrodes. In each case, one electrode is active while the remaining two act as a reference. Electrical pulse delivery and the corresponding relaxation curve measurements are continually cycled through the three possible electrode combinations. This feature allows the detection of conditions which result in an asymmetrical charge imbalance between electrodes, such as partial contact. In addition, electrode cycling minimizes electrochemical degradation. Each tissue observation incorporates several relaxation curves recorded for each of the three electrode configurations. After each series of measurements an electrode discharge cycle is implemented.

Figure 8A:
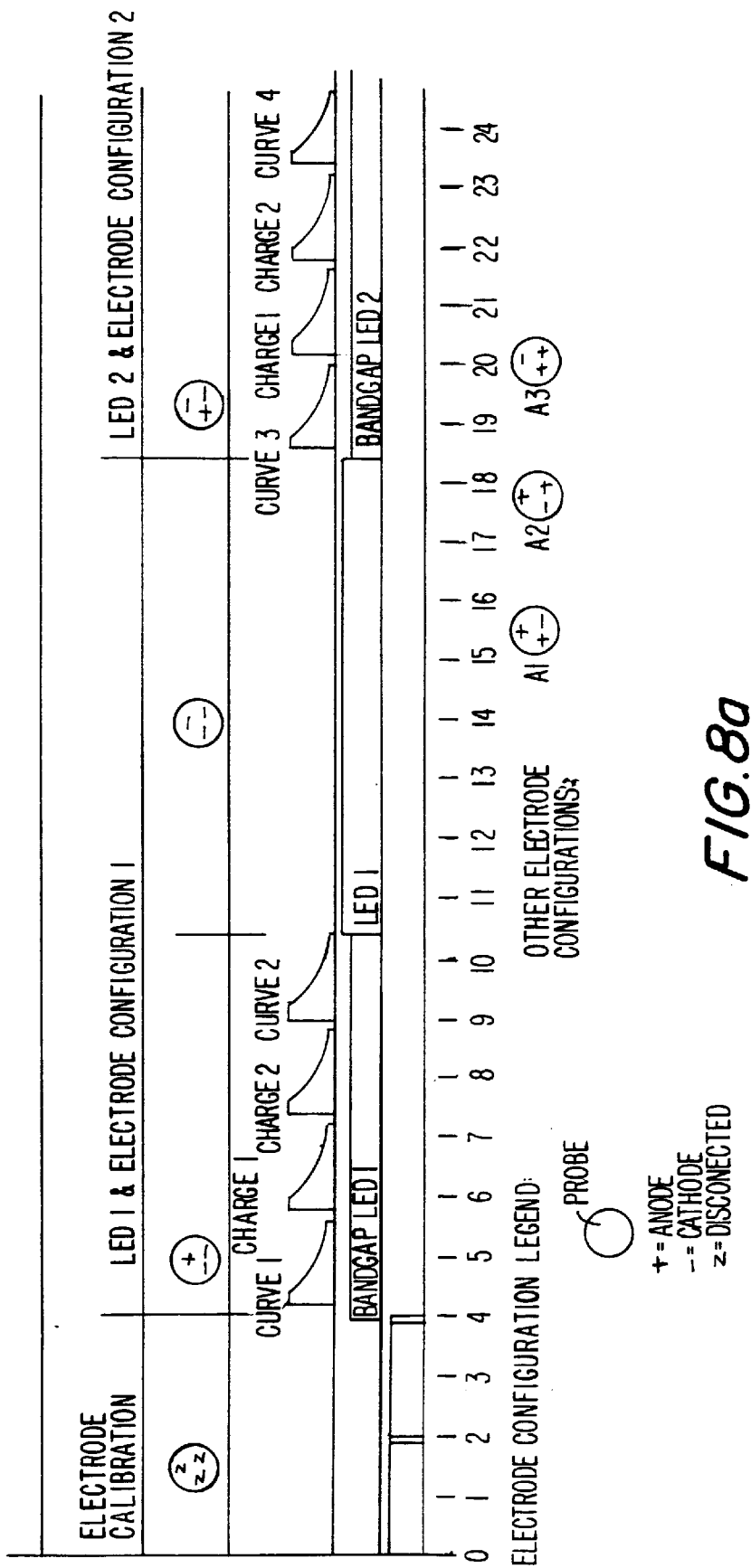
FIGS. 8a–8c are timing diagrams for the optical and electrical measurements made during a measurement cycle.
Figure 8B:
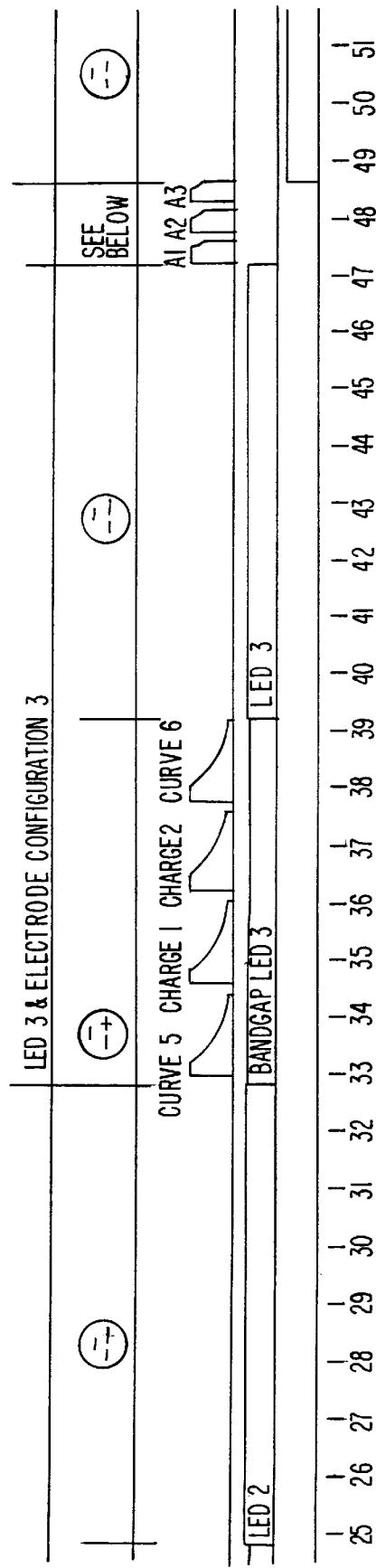
Figure 8C:
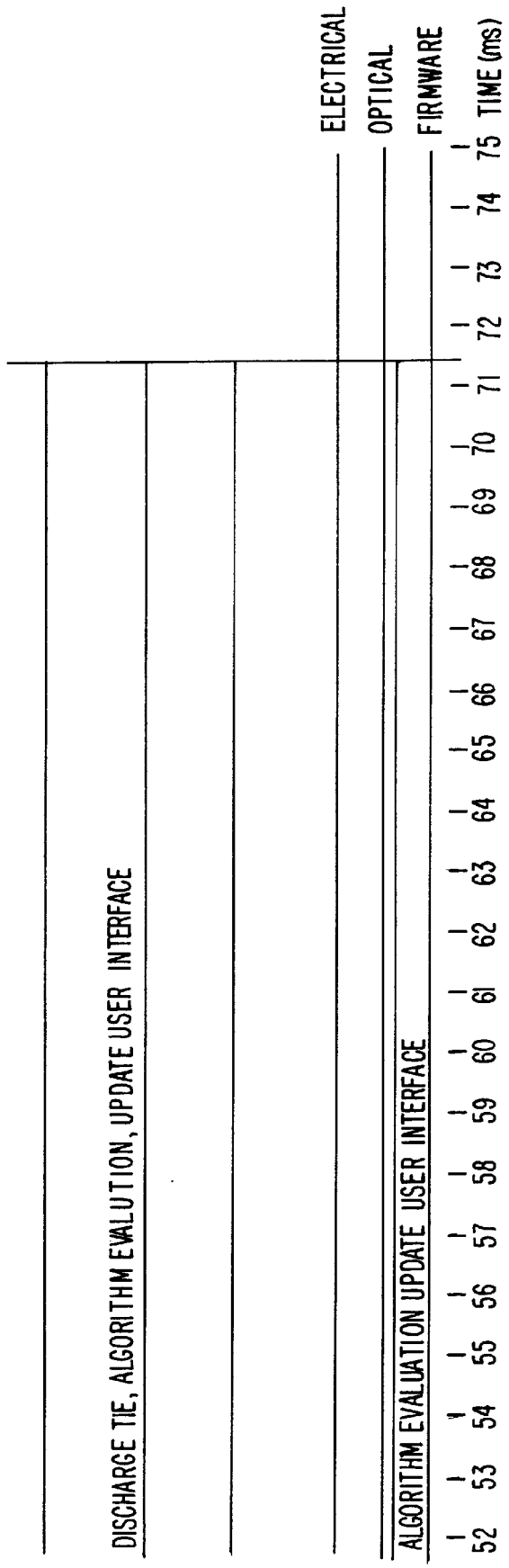

FIGS. 8a–c show a typical three electrode measurement cycle, which takes 71.43 ms, i.e. 14 cycles per second, and is divided into nine intervals. During the first ("calibration") interval (0–4 ms) an internal calibration of the instrument takes place. Calibration of the console is adjustment of the console's electronics so its performance and behavioral characteristics are consistent between consoles. Calibration of the electrical offsets is to eliminate probe variation due to different probes and temperature variation as well as to reduce the need for factory calibration. This calibration step enables less costly and lower power circuitry to be used. Electrode circuitry calibration is carried out by applying a test signal to the probe, and then measuring this value with an analog to digital converter and adjusting the offset using a digital to analog converter until the correct value is obtained. The calibration is carried out under microprocessor control. This method is a successive approximation type of search which reduces the calibration time from $2^n$ iterations to n+1 iterations. This is depicted schematically as three disconnected terminals in a circle in FIG. 8a.

Figure 6:
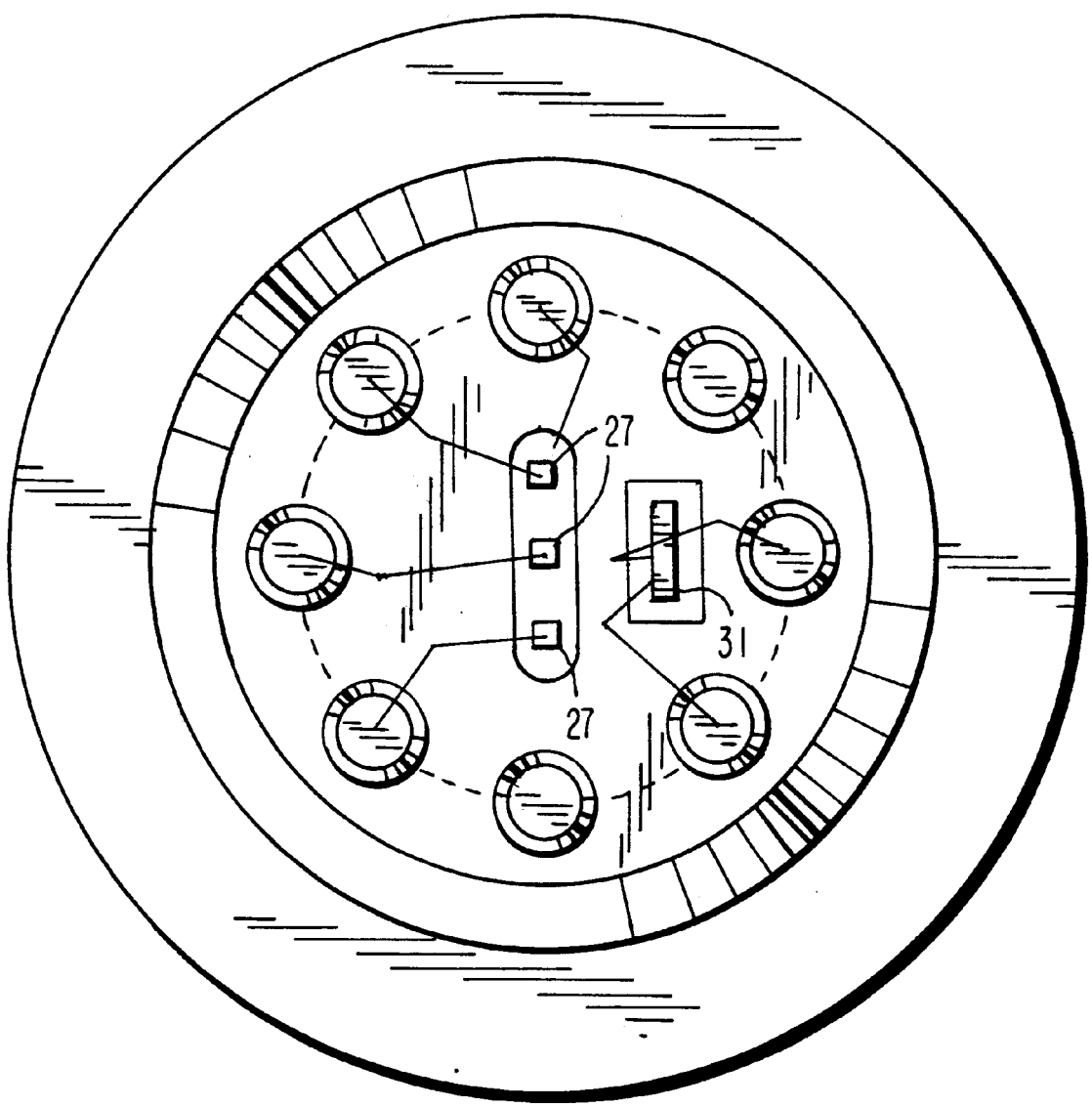
FIG. 6 is a top view of the probe tip in a preferred embodiment having a photodiode at the probe tip.
Figure 7:
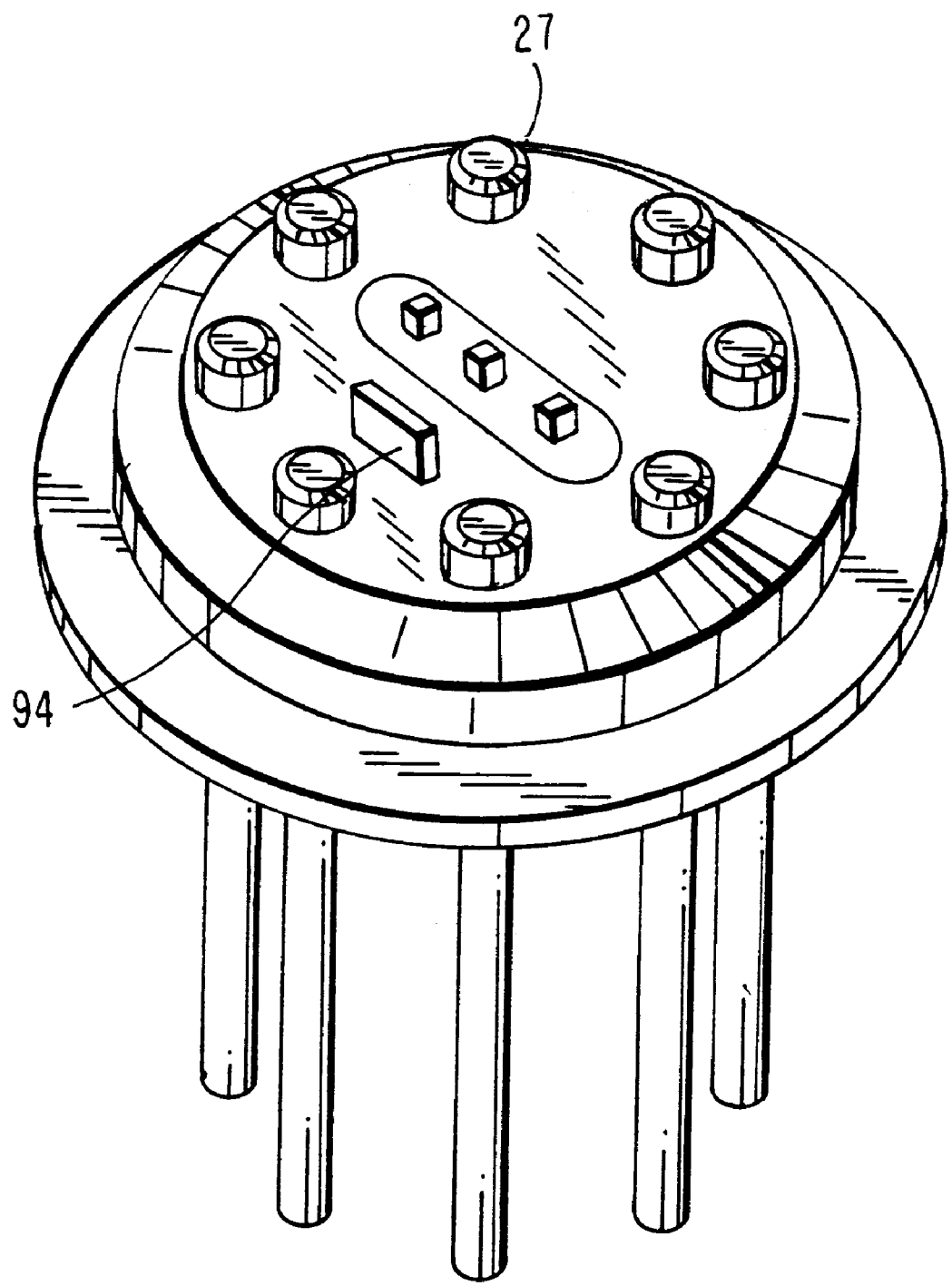
FIG. 7 is a perspective view of the probe tip of FIG. 6.

During the $2^{nd}$, $4^{th}$, and $6^{th}$ ("current measurement") intervals (4–10.5 ms; 18.5–25 ms; 32.5–39 ms), a current (the inrush current) is injected respectively from one of the three possible probe tip electrode configurations (in which one electrode is at anode potential and two are cathodes). The temperature of one of the three LEDs is determined at the same time. The forward bias voltage of a semiconductor diode is temperature dependent. This temperature dependence is due to the variation in the semiconductor bandgap. The optical output of an LED is also temperature dependent. To make accurate measurements of the backscattered light from the cervix, the output of the light source needs to be either constant or known. The optical output of an LED can be determined by the LED's temperature and drive current if that LED has been characterized. The need for determining the temperature of the LED light source is critical as the short term environmental temperature changes are likely to exceed 20° C. The optical output of uncompensated LEDs are likely to vary by more than 20% under these conditions leading to a very inaccurate measure of backscattered light. The temperature of an LED junction can be determined by measuring its bandgap related potential, that is, the forward bias with a known current thus avoiding the need for a separate temperature sensor for each LED. The present invention's novel approach of leaving the LED's optical output unregulated and compensating the detector's gain is superior to prior techniques for compensating LED output, e.g. Mroczka Janusz et al., "Methods of temperature stabilization of light-emitting diode radiation", Rev. Sci. Instrum. Vol. 65, No. 4, April 1994, as it removes the chance of instability in the LED servo loop. Temperature, however, is not the only factor than can affect the output intensity of the LED. Aging of the LED affects its output as well. Therefore an alternative embodiment is depicted in FIGS. 6 and 7 in which another photodetector 94 is positioned adjacent to the LED dice and receives light from each of the LED's directly without light fiber connections. An advantage of this alternative embodiment is that the intensity of the light may be measured and corrected using signals that are detected while the LEDs are being pulsed rather than using data from a separate measurement as is done for the bandgap. Where instantaneous correction is not desired during each pulsing sequence the average intensity could be corrected using accumulated data.

During the 3rd, $5^{th}$ and $7^{th}$ ("optical measurement") intervals (10.5–18.5 ms, 25–32.5 ms, 39–47 ms), one of the three LEDs whose temperature has been determined emits light the backscattering of which is simultaneously detected.

During the $8^{th}$ ("probe orientation') interval (47–48.5 ms), the proper orientation of the probe against the tissue surface is checked.

During the $9^{th}$ ('discharge") interval (48.5–71.5 ms), the surface under examination is discharged, the data analysis algorithm is executed, and the user interface is updated.

During each of the three current measurement intervals four square current pulses of approximately 250 µs duration are employed, separated by 1.8 ms. Three measurements are made of the decay amplitude of each of the first and fourth current pulses during the time prior to the second pulse or prior to the end of the current measurement interval. Thus a series of 18 electrical measurements of pulse decay are made in each 71.43 µs cycle. A set of parameters is generated to parameterize the shape of the inrush current and voltage decay curves in each interval such as with a multiple exponential best fit.

Alternative shape parameterizations include transforming the data with ordinate and abscissa operators such that they become piecewise straight line segments. Such operators include taking logs so as to produce log/log displays, using inverse time as the abscissa or any other transformations that provide good fit to the data. Parameters associated with the transformed functions can then be associated with the degree of tissue abnormality. Typical operations that can be applied to the curves and variables that can be extracted for use as discriminants are as follows:

1. The slope and intercept of the log voltage/inverse time plot of the curves.

2. The slope and intercept of the long voltage/log time plot of the curves.

3. The subtraction, addition, multiplication or division of or by a function to diminish the a priori known obscuration effect of some artifact of, or noise source within the system.

4. The slope of the voltage vs. current curve at the start of the relaxation curve.

5. The relationship between the parameters of the inrush current curve and the parameters of the relaxation curve.

6. The use of integrals of segments of the curves based on time intervals.

7. The use of integrals of segments of the curves based on voltage intervals.

8. The use of integrals of segments of the curves based on current intervals.

9. The magnitudes of the offsets.

The discriminants as listed under item 6 above are the ones presently preferred.

A total of 21 tissue classification parameters (18 electrical and 3 optical) are extracted from the digitized optical and electrical data, in addition to various parameters extracted for the detection of poor contact conditions. Some of the electrical parameters are functions derived from various portions of the measured relaxation curves. These parameters are then passed to the processor chip for classification. With 21 parameters processed per observation, the total rate of parameter processing is 294 per second. Assuming that 1000 observations are processed per patient, the total number of parameters under consideration is approximately 20,000.

Thus the apparatus of the present invention categorizes biological tissue by having a probe tip able to select a tissue surface area by contact and applying a group of sequential current pulses from the probe tip to each of a succession of selected tissue surface areas. The sequential pulses occur within groups that occur at a rate fast enough so that they are applied to substantially the same tissue surface area. A circuit then derives values for a group of parameters that indicate the response to the group of sequential current pulses applied to each selected tissue surface area. A memory stores a catalog of tissue types that are associated with respective subsets of groups of parameter values. The processor then compares the group of parameter values that indicate the response of the selected tissue surface area with the stored subsets of groups of parameter values to categorize the tissue surface area.

The parameters in the parameter group are not necessarily associated on a one-to-one basis with the sequential current pulses in the current pulse group. As shown in FIGS. 8*a–c*, the successive groups of sequential current pulses may be separated in time from each other by a time interval substantially greater than the time interval between the sequential current pulses within an individual group.

Also as seen in FIGS. 8a–c during any current pulse for which a tissue response is desired multiple measurements of the tissue potential are taken during decay of the potential following application of the current pulse. Furthermore, the system permits at least two parameter values to be derived during the potential decay following each current pulse for which a tissue response is desired thereby allowing a more sophisticated parameterization of the current decay than a simple exponential. Enough measurements are made during the current decay so that each of the parameters may be derived from several of the multiple measurements taken during the decay of the current pulse for which a tissue response is desired. These multiple parameters are then available so that the processor can categorize any tissue surface in accordance with at least two parameter values derived during the potential decay following each of at least two current pulses. In general these two current pulses are separated by at least one other current pulse which is not used by the processor to categorize the tissue.

In the above description which is based on a three electrode probe configuration, the aforementioned pulses are applied by three electrodes. This is done so that non-overlapping current pulses flow between different groups of electrodes and corresponding current pulse applications and measurement cycles occur for different groups of electrodes. Similarly, corresponding parameter values derived following the current pulses for different groups of electrodes are combined for the categorization of the tissue surface area by the processor. Other electrode configurations, for example, two or four, would require modifications to the sequence as described.

It is preferred that the optical and electrical measurements on the same tissue be interspersed and that the charge dissipation in the tissue volume underneath a selected tissue surface is not complete by the time the next sequential current pulse is applied. This results in the categorization of the selected tissue being dependant upon the particular order of the electrical measurements. This more complex probing by electrical pulses creates a more subtle response to the probing and allows greater discrimination of tissue characteristics. Nevertheless, the pulses are preferably separated in time from each other by a time interval substantially greater than the time interval between sequential current pulses within an individual group so that the categorizations of successive selected tissue surface areas are substantially independent of each other.

Averaging of Test Results.

The timing of the various events aids the diagnostic abilities of the invention. In particular it is believed that by measuring only the decay characteristics of the first and fourth current pulse in each current measurement interval, two different physical characteristics of the tissue under examination are characterized. The first pulse provides the response of the tissue to a current pulse after the tissue has had an opportunity to discharge from the previous measurement interval. Indeed the first pulse of the first measurement interval has had the longest time to recover and perhaps to recover completely. It has been conjectured that the different timing of the pulse recovery times permits tissue at different depths below the surface to influence the measured parameter values. The cumulative effect of these different recovery times is determined in the present invention by averaging the responses. Thus some information is lost, but a wider range of effects influence the final result. In an alternative embodiment this averaging is not performed and the greater information content is utilized.

Allowing Tissue Charge from Prior Tests to Dissipate.

The timing of the various electrical measurements into intervals separated by optical measurement intervals allows a short recovery time after each current measurement interval. Furthermore the lengthy discharge interval permits a more total recovery of the tissue so that individual cycles can maintain independence from one another. To aid in the complete discharge, during the discharge interval the three electrical probe tip elements are made active cathodes and kept at low impedance. This is quite contrary to the normal construction of measuring electrodes where the impedance is kept high so that the current characteristics of the object being measured are effectively isolated from the current flow in the measuring instrument. Essentially the benefit of isolation is traded off for the rapidity of recovery of the tissue for the next measurement cycle.

Reducing Overall Observation Time by Order of Test Performance.

The order of performance of the optical and the electrical tests also has the beneficial effect of reducing the overall observation time required for each measurement. Thus the inactive period between electrical measurements is used for the optical measurements and vice versa. The measurement of LED bandgap potential and the subsequent compensation for temperature variation characterized by the bandgap potential requires little computational bandwidth and does not interfere with the rapidity of measurement necessary to characterize each electrical decay curve. In this example, only eight readings are shown as being taken of the current flow into the electrodes (the inrush current) during the early part of the 250 µs applied pulse. When it is desired to make additional use of the inrush current readings, it will be appropriate to take current readings throughout the 250 µs pulse.

FIG. 9 depicts an individual voltage relaxation curve. As indicated an initial offset voltage is determined by eight consecutive observations sampled at 9 µs intervals. The height of the square wave pulse is similarly measured by eight consecutive observations sampled at 9 µs intervals. During the voltage decay samples are taken at 9 µs intervals, but not all are recorded. FIG. 9 also shows the corresponding current relaxation curve. In this example, only eight readings are shown as being taken of the current flow into the electrodes (the inrush current) during the early part of the 250 µs applied pulse. When it is desired to make additional use of the inrush current readings, it will be appropriate to take current readings throughout the 250 µs pulse.

Distinct Values from Two Different Decay Curves.

The use of the first and fourth electrical measurement in each set of four as distinct variables without averaging allows recovery of the maximum amount of information from the electrical measurements. This information is utilized in the statistical analysis of the electrical and optical data.

During the optical measurement intervals data is collected and the optical system measures the bandgap potential of a first LED by applying a small current to the LED and measuring the potential across it. This provides a readout of the temperature of the LED and permits correction for temperature variation to be made.

The results of the tests are displayed to the physician operating the probe by a series of display lights. These are depicted in FIG. 3. A summary diagnosis of the tissue under the probe tip and user error status is provided by the diagnosis lamps 61 on the back 63 of the probe (seen in FIG.

3). These diagnosis lamps face the clinician in normal use. The pattern of lights signaling different conditions is as follows:

| CONDITION | LED 1 | LED 2 | LED 3 | LED 4 | LED 5 |
|---|---|---|---|---|---|
| Color | Green | Red | Blue | Blue | Blue |
| System OK | on | on/off | on/off | on/off | on/off |
| System Error | off | off | off | off | off |
| Unable to Diagnose | on | off | off | off | off |
| Operator Error | on | on | off | off | off |
| Normal Tissue | on | off | on | off | off |
| Low Grade Lesion | on | off | on | on | off |
| High Grade Lesion | on | off | on | on | on |

The meaning of these conditions is as follows:

i. High-grade Lesion: (inclusive of CIN2, CIN3, HGSIL, microinvasive and invasive cancer)

ii. Low Grade Lesion: (inclusive of CIN1, LGSIL, atypia, ASCUS, HPV, necrosis)

iii. Normal: (inclusive of OSE, columnar, immature metaplasia, mature metaplasia and nabothian follicle, regenerative tissue, atrophic tissue)

iv. Unable to Diagnose: (this category includes data outside the scope of the algorithm or within overlapping boundaries between tissue groupings)

v. Operator Error: (inclusive of lift off, bad angle, slip error and saturation)

A 6th signaling category indicates whether the device is working within specifications.

The particular color regime has been chosen because green is conventional for OK and system on, red is conventional for error or malfunction and blue to maximize peripheral vision stimulation, viz. the outer retina has a higher concentration of rod cells, which have greatest sensitivity to blue light. If the operator is focused on the tip of the probe then the indicator LEDs will be sighted by peripheral vision. Thus, the method of signaling a diagnosis is via four approaches, namely, the display on the console, LED indicators on the rear of the probe, audible tones via headphones and a summary printout of the diagnosis. For this purpose, the console display mimics that of the LED output with the addition of labeling. In this way the console will serve as an alternative display of diagnosis and as a reference to the meaning of the LED configuration on the rear of the probe. The audible signal also follows the same pattern as the LED output, however, using tones, for example, the tones will shift to a higher pitch for a more significant classification. The printout summarizes the diagnosis.

The algorithm first checks for poor contact, and if detected, the operator is signaled via the probe handle lights and the console, and no diagnosis is attempted. As the process is repeated at a rate of 14 times per second, the operator receives instantaneous feedback on the probe position and may adjust device positioning accordingly. The poor contact check includes the following conditions: (1) the probe being at an angle to the cervix; (2) the probe partially or fully lifting off the cervix, or lift-off; (3) the probe moving too quickly across the cervix for accurate measurements to be performed, or slip; and (4) the probe is positioned over a junction between tissue types. The angle and junction conditions are detected through an imbalance in the electrical parameters, while the lift-off condition is detected by means of out of range electrical and optical readings.

If the data pass the poor contact check, then diagnosis into one of 17 tissue types in the following table is attempted:

| | High Grade Squamous Intraepithelial Lesions (HSIL) / Invasive Cancer (IC) |
|---|---|
| 1 | Carcinoma |
| 2 | Cervical Intraepithelial Neoplasia (CIN) 3 |
| 2* | CIN 3 with an immature metaplasia component |
| 3 | CIN 2 |
| 3* | CIN 2 with an immature metaplasia component |
| | Low Grade Squamous Intraepithelial Lesions (LSIL) |
| 4 | Acetowhite epithelium with or without HPV stigmata |
| 5 | Acetowhite epithelium with vessels and HPV stigmata |
| 6 | Acetowhite epithelium within immature metaplasia (atypia) |
| | Original Squamous Epithelium (OSE) with HPV Stigmata |
| 7 | OSE with HPV stigmata Acetowhite epithelium + |
| 8 | OSE with HPV stigmata Acetowhite epithelium + + |
| 8a | OSE with HPV stigmata Acetowhite epithelium + + with vessels |
| 8b | OSE with HPV stigmata Acetowhite epithelium + + with surface contour changes |
| 9 | OSE with HPV stigmata with micropapilliary changes (not Acetowhite) |
| | Normal: |
| 10 | Original squamous epithelium |
| 11 | Columnar epithelium |
| 12 | Immature Metaplasia, physiologic |
| 13 | Intermediate metaplasia |
| 14 | Mature metaplasia |
| 15 | Regenerate squamous epithelium (post treatment) |
| | Other: |
| 16 | Cervicitis (acute/subacute) |
| 17 | Atrophy |

An initial validity check on the data is performed to ensure that the multivariate data distribution is within the limits of all valid classifier data. If the result signals one out of range, then no diagnosis will be made and the operator is signaled.

A most probable tissue type is then selected. A further validity check is performed to ensure that the multivariate data distribution is within the limits of all valid classifier data for the selected tissue type. Again, if the reading proves to be an outlier, no diagnosis is performed and the operator is signaled. The probability estimate (certainty of assignment to a particular tissue type) is then assessed against a pre-defined decision threshold. If the probability estimate is below the threshold, no diagnosis is performed. Again, because the measurements occur at the rate of 14 per second, the operator receives instant feedback. If the estimate is above the decision threshold, a diagnosis is made, the tissue grouped into pre-selected categories, for example, Cancer or High Grade Abnormality (HSIL), Low Grade Abnormality (LSIL) and Normal, and the operator is signaled with the result.

There are two levels at which the probe classification algorithm involves a pre-determined decision-making process affecting the "trade off" between the sensitivity and specificity of the test. The pre-determined decision thresholds define Receiver Operating Characteristic (ROC) curves. The ROC curve is a graphical description of test performance representing the relationship between the true positive fraction (sensitivity) and the false positive fraction (1−specificity). An increase in the decision threshold will cause an overall increase in device specificity at the expense of sensitivity, and vice versa.

The first level decision threshold concerns the probability estimate used for the classification of tissue into one of 17 types. The second level decision threshold concerns the grouping of tissue types into categories, whereby the grouping can be adjusted, depending on the desired outcome of the screening test. Appropriate adjustment of the decision threshold allows the configuration of an optimal trade off between sensitivity and specificity, with a particular focus on the cut-off between low grade changes and minor atypia.

Safety and Reliability of the System

A number of features have been developed to ensure the safety of the patient and long term reliability of the probe system. These include calibration procedures, temperature compensation and electrical safety precautions.

It is necessary to calibrate each probe during manufacture in order to ensure that optical and electrical output signals are the same for each device. Optical calibration is performed in a turbid solution of stable optical characteristics with an optical spectral distribution chosen to simulate that of cervical tissue, and electrical calibration is performed using a stable electrolyte solution. An optical calibration check is also performed at the beginning of each clinical session. The operating temperature of the probe is 5 to 50 degrees Celsius. Temperature compensation of the LEDs is necessary since the optical measurements are extremely sensitive to the ambient temperature. Stability of operation across the required temperature range is achieved by continuous automatic measurement of the temperature and compensatory adjustment. Electrical safety of the patient has been a prime consideration in the design of the device, and a number of design techniques have been employed, including electrical isolation from the mains voltage, double insulation for all parts not applied to the patient, a small voltage employed for the delivered pulses, "watchdog" monitoring systems including continual voltage monitoring of the delivered pulses, LED protection circuitry and the employment of low voltages throughout the probe and console.

The development of the classification algorithm is an ongoing process and the clinical database used as the basis of algorithm construction should be continually refined. This process may proceed as follows:

Data for algorithm development is collected for several thousand women. The database includes a number of data subsets for each tissue type and for Poor Contact conditions, including contact problems induced by excess cervical mucus or blood.

Data collection for algorithm development proceeds by means of a data collection system incorporating a link from the console to a computer for the download of digitized data, and a video mixer, recorder and printer. Probing is performed, followed by formal colposcopy with aqueous acetic acid staining of the cervix, and the session is recorded on video. A colpophotograph is taken after acetic acid staining, and the colposcopist marks the diagnosis of all tissue types present on the photograph. Patient history and current status information, including Pap smear, colposcopy and biopsy results are recorded on a clinical record form and subsequently entered into the probe database. Following the data collection session, the data are analyzed in the laboratory by viewing the probe session video concurrently with a display of optical and electrical parameters. Colposcopy and biopsy results from participating clinics are subject to a uniform review process in order to reconcile colposcopic and histological diagnoses. Briefly, video images taken during the colposcopy session and histology results, if available, are reviewed by an independent colposcopist. Referral to a second colposcopist is performed in cases of an initial abnormal diagnosis and in cases of doubt. Where a reference diagnosis cannot be established, data are excluded from the algorithm database.

The 17 tissue classification categories are used in the establishment of the Reference Diagnosis. Tissue type classification is based on the colposcopic classification of Coppleson, Pixley and Reid (Coppleson M, et al. "Colposcopy: A scientific and practical approach to the cervix, vagina and vulva in health and disease", Third Ed. Thomas, 1986), and the Reid and Scalzi abnormality grading system (Reid R et al., "An improved colposcopic index for differentiating benign papillomaviral infections from high grade cervical intraepithelial neoplasia" Am J Obstet Gynecol 1985: 153(6), 611–8).

The present invention is designed to be a screening, rather than a diagnostic tool. Therefore, the tissue types are grouped into categories which are of use for the clinician when making the referral decision. These categories are: Probe Cancer or High Grade Abnormality; Probe Low Grade Abnormality; and Probe Normal. Note that the tissue types identified as original squamous epithelium with HPV stigmata (tissue types 7 to 9) may potentially be grouped into either of the output categories of Probe Low Grade Abnormality or Probe Normal, depending upon the desired screening result. The two options effectively correspond to alternative operating points on the device receiver operating characteristic.

As previously described, the programmable gain synchronous detector 35 receives the raw optical signal and provides output to the tissue type classifier 37. Synchronous detection is a demodulation process in which the original signal is recovered from a noisy transmission path by multiplying the modulated signal by the output of a synchronous oscillator locked to the carrier. This technique traditionally is used in the communications field for demodulation of amplitude modulated signals. Many sources of interference are present when making measurements of the backscattered light from the cervix. These sources of interference are both electrical and optical in nature. Notably, the luminous intensity of colposcope light is far greater than of the light source used by the probe. Until synchronous detection was employed, the signal chain would often saturate. Synchronous detection has allowed the reduction of interference by limiting the bandwidth of the processing chain while using modest levels of probe light.

Figure 10:
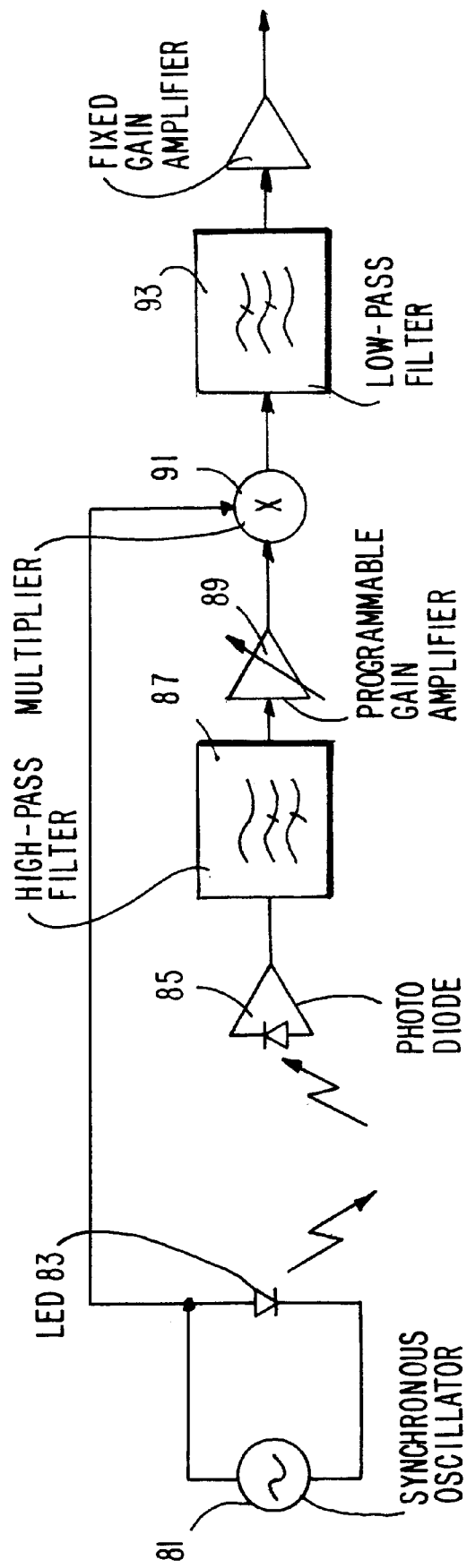
FIG. 10 is a block diagram of the synchronous detection system employed in the present invention.

FIG. 10 is a block diagram of the synchronous detection system employed in the present invention. The synchronous oscillator 81 provides both the drive for a typical LED 83 and the synchronizing signal for the detector. The oscillator's frequency is 4 kHz and is thus away from the frequencies of the most common noise sources. The photodiode 85 is used to detect the backscattered light from the cervix. The photodiode is located in the probe along with a low gain transimpedance amplifier. The gain of this stage is kept low to avoid saturation by ambient light sources. The return signal is accompanied by two common noise sources. The first is lighting ripple from an illumination source like a colposcope, the second is random thermal noise. The high pass filter 87 is used to remove the steadystate light. It is also effective for reducing the low frequency ripple component from the colposcope illumination, thus avoiding saturation of the following signal processing stages. The programmable gain amplifier 89 is used to normalize variations in the LED's optical output. The multiplier 91 correlates the real signal component of the photodiode signal while randomizing the noise component. The low pass filter 93 takes the multiplied signal and provides an average. This helps separate the correlated signal from the uncorrelated signal (noise). The lowpass filter also sets the bandwidth of the signal processing chain. The lower the cut-off frequency the more narrow the bandwidth and hence the greater the rejection. However, if the bandwidth is made too narrow then the system will take a long time to respond. Rather than the traditional integrator or first-order low-pass filter, a high order Bessel filter has been used in the probe's synchronous detector, thus giving excellent out-of-band noise rejection as well as good transient performance.

Although the invention has been described in terms of specific embodiments, it is intended that the patent cover equivalent substitutions for any of the elements of these embodiments, and that the protection afforded by this patent be determined by the legitimate scope of the following claims:

What is claimed is:

1. An apparatus for categorizing biological tissue whose surface area is selected by contact comprising:
    a probe tip having an end surface that contacts said tissue surface area,
    a potential source for applying a group of sequential current pulses from said probe tip to each of successively selected tissue surface areas, the sequential pulses within each group occurring at a rate fast enough so that they are applied to substantially the same tissue surface area,
    a circuit for deriving values for a group of parameters indicative of the response to the group of sequential current pulses applied to each selected tissue surface area,
    a memory adapted to store a catalog of tissue types associated with respective subsets of groups of parameter values, and
    a processor for comparing the group of parameter values indicative of the response of a selected tissue surface area with the stored subsets of groups of parameter values to categorize said tissue surface area, wherein the parameters in said parameter group are not associated on a one-to-one basis with the sequential current pulses in said current pulse group.

2. An apparatus in accordance with claim 1 wherein successive groups of sequential current pulses are separated in time from each other by a time interval substantially greater than the time interval between the sequential current pulses within an individual group.

3. An apparatus for categorizing biological tissue whose surface area is selected by contact comprising:
    a probe tip having an end surface that contacts said tissue surface area,
    a potential source for applying a group of sequential current pulses from said probe tip to each of successively selected tissue surface areas, the sequential pulses within each group occurring at a rate fast enough so that they are applied to substantially the same tissue surface area,
    a circuit for deriving values for a group of parameters indicative of the response to the group of sequential current pulses applied to each selected tissue surface area,
    a memory adapted to store a catalog of tissue types associated with respective subsets of groups of parameter values, and
    a processor for comparing the group of parameter values indicative of the response of a selected tissue surface area with the stored subsets of groups of parameter values to categorize said tissue surface area,
    wherein, for any current pulse for which a tissue response is desired, multiple measurements of the tissue potential are taken during decay of the potential following application of the current pulse,
    wherein at least two parameter values are derived during the potential decay following each current pulse for which a tissue response is desired,
    wherein each of said at least two parameter values is derived from several of the multiple measurements taken during decay of the current pulse for which a tissue response is desired,
    wherein said processor categorizes any tissue surface area in accordance with at least two parameter values derived during the potential decay following each of at least two current pulses, and wherein said at least two current pulses are separated by at least one other current pulse the tissue response to which is not used by said processor to categorize the tissue to which said current pulses are applied.

4. An apparatus for categorizing biological tissue whose surface area is selected by contact comprising:
    a probe tip having an end surface that contacts said tissue surface area,
    a potential source for applying a group of sequential current pulses from said probe tip to each of successively selected tissue surface areas, the sequential pulses within each group occurring at a rate fast enough so that they are applied to substantially the same tissue surface area,
    a circuit for deriving values for a group of parameters indicative of the response to the group of sequential current pulses applied to each selected tissue surface area,
    a memory adapted to store a catalog of tissue types associated with respective subsets of groups of parameter values, and
    a processor for comparing the group of parameter values indicative of the response of a selected tissue surface area with the stored subsets of groups of parameter values to categorize said tissue surface area,
    wherein, for any current pulse for which a tissue response is desired, multiple measurements of the tissue potential are taken during decay of the potential following application of the current pulse,
    wherein at least two parameter values are derived during the potential decay following each current pulse for which a tissue response is desired, and
    wherein said probe tip has at least three electrodes for applying current pulses to a selected tissue surface area with non-overlapping current pulses flowing between different groups of said electrodes, corresponding current pulse application and measurement cycles occurring for different groups of said electrodes, and corresponding ones of the at least two parameter values derived following the current pulses for different groups of said electrodes being combined for the categorization of said tissue surface area by said processor.

5. An apparatus in accordance with claim 4 wherein categorization of a tissue surface area by said processor is deemed unreliable if the difference between any two corresponding parameter values derived following the current pulses for different groups of said electrodes exceeds a threshold value.

6. An apparatus for categorizing biological tissue whose surface area is selected by contact comprising:

a probe tip having an end surface that contacts said tissue surface area, a potential source for applying a group of sequential current pulses from said probe tip to each of successively selected tissue surface areas, the sequential pulses within each group occurring at a rate fast enough so that they are applied to substantially the same tissue surface area, a circuit for deriving values for a group of parameters indicative of the response to the group of sequential current pulses applied to each selected tissue surface area, a memory adapted to store a catalog of tissue types associated with respective subsets of groups of parameter values, and a processor for comparing the group of parameter values indicative of the response of a selected tissue surface area with the stored subsets of groups of parameter values to categorize said tissue surface area, wherein, for any current pulse for which a tissue response is desired, multiple measurements of the tissue potential are taken during decay of the potential following application of the current pulse, wherein at least two parameter values are derived during the potential decay following each current pulse for which a tissue response is desired, and wherein said probe tip has at least three electrodes for applying current pulses to a selected tissue surface area with non-overlapping current pulses flowing between different groups of said electrodes, corresponding current pulse application and measurement cycles occurring for different groups of said electrodes, and said electrodes are connected in sequential groups to apply sequential current pulses to a selected tissue surface area such that electrode degradation by electrochemical effects is minimized.

7. An apparatus for categorizing biological tissue whose surface area is selected by contact comprising:

a probe tip having an end surface that contacts said tissue surface area, a potential source for applying a group of sequential current pulses from said probe tip to each of successively selected tissue surface areas, the sequential pulses within each group occurring at a rate fast enough so that they are applied to substantially the same tissue surface area, a circuit for deriving values for a group of parameters indicative of the response to the group of sequential current pulses applied to each selected tissue surface area, a memory adapted to store a catalog of tissue types associated with respective subsets of groups of parameter values, and a processor for comparing the group of parameter values indicative of the response of a selected tissue surface area with the stored subsets of groups of parameter values to categorize said tissue surface area, wherein said probe tip having electromagnetic radiation transmitting components to perform optical measurements on the selected tissue surface area, and multiple interspersed optical and electrical measurements are performed on the same tissue surface area selected by said probe.

8. An apparatus for categorizing biological tissue whose surface area is selected by contact comprising:

a probe tip having an end surface that contacts said tissue surface area, a potential source for applying a group of sequential current pulses from said probe tip to each of successively selected tissue surface areas, the sequential pulses within each group occurring at a rate fast enough so that they are applied to substantially the same tissue surface area, a circuit for deriving values for a group of parameters indicative of the response to the group of sequential current pulses applied to each selected tissue surface area, a memory adapted to store a catalog of tissue types associated with respective subsets of groups of parameter values, and a processor for comparing the group of parameter values indicative of the response of a selected tissue surface area with the stored subsets of groups of parameter values to categorize said tissue surface area, wherein the charge dissipation in the tissue volume underneath a selected tissue surface area is not complete by the time the next sequential current pulse is applied so that the categorizations of selected tissue surface areas are functions of the particular order of the electrical measurements.

9. An apparatus in accordance with claim 8 wherein successive groups of sequential current pulses are separated in time from each other by a time interval substantially greater than the time interval between sequential current pulses within an individual group so that the categorizations of successive selected tissue surface areas are substantially independent of each other.

10. An apparatus for categorizing biological tissue whose surface area is selected by contact comprising:

a probe tip having an end surface that contacts said tissue surface area, a potential source for applying a group of sequential current pulses from said probe tip to each of successively selected tissue surface areas, the sequential pulses within each group occurring at a rate fast enough so that they are applied to substantially the same tissue surface area, a circuit for deriving values for a group of parameters indicative of the response to the group of sequential current pulses applied to each selected tissue surface area, a memory adapted to store a catalog of tissue types associated with respective subsets of groups of parameter values, and a processor for comparing the group of parameter values indicative of the response of a selected tissue surface area with the stored subsets of groups of parameter values to categorize said tissue surface area, wherein the charge dissipation in the tissue volume underneath a selected tissue surface area is not complete by the time the next sequential current pulse is applied so that the categorizations of selected tissue surface areas are functions of the timings between sequential current pulses.

11. An apparatus for categorizing biological tissue whose surface area is selected by contact comprising:

a probe tip having an end surface that contacts said tissue surface area, a potential source for applying a group of sequential current pulses from said probe tip to each of successively selected tissue surface areas, the sequential pulses within each group occurring at a rate fast enough so that they are applied to substantially the same tissue surface area, a circuit for deriving values for a group of parameters indicative of the response to the group of sequential current pulses applied to each selected tissue surface area, a memory adapted to store a catalog of tissue types associated with respective subsets of groups of parameter values, and a processor for comparing the group of parameter values indicative of the response of a selected tissue surface area with the stored subsets of groups of parameter values to categorize said tissue surface area, wherein said circuit for deriving said group of parameter values performs measurements on a selected tissue surface area by using a low-impedance probe whose influence on the decay of the potential in the underlying tissue volume following application of a current pulse is sufficiently great that valid categorization of a selected tissue surface area requires use of a comparable probe during the prior derivation of said catalog of tissue types.

12. An apparatus for categorizing biological tissue whose surface area is selected by contact comprising:

a probe tip having an end surface that contacts said tissue surface area, a potential source for applying a group of sequential current pulses from said probe tip to each of successively selected tissue surface areas, the sequential pulses within each group occurring at a rate fast enough so that they are applied to substantially the same tissue surface area, a circuit for deriving values for a group of parameters indicative of the response to the group of sequential current pulses applied to each selected tissue surface area, a memory adapted to store a catalog of tissue types associated with respective subsets of groups of parameter values, and a processor for comparing the group of parameter values indicative of the response of a selected tissue surface area with the stored subsets of groups of parameter values to categorize said tissue surface area, wherein said probe tip further having optically coupled to it at least one light-emitting diode and a detector for detecting the light scattered back from the selected tissue surface area, the apparatus further comprising a circuit for measuring the bandgap potential of the light-emitting diode and adjusting accordingly the gain of the amplifier handling the signal from said detector to compensate for temperature fluctuations.

13. An apparatus in accordance with claim 12 wherein multiple interspersed optical and electrical measurements are performed on the same tissue surface area selected by said probe, and the bandgap potential of said at least one light-emitting diode is measured during the course of deriving values for said group of parameters.

14. An apparatus in accordance with claim 13 wherein said probe tip has at least three electrodes for applying current pulses to a selected tissue surface area with non-overlapping current pulses flowing between different groups of said electrodes, corresponding current pulse application and measurement cycles occurring for different groups of said electrodes, and all of said electrodes are connected together electrically during the intervals between said sequential current pulses.

15. An apparatus for categorizing biological tissue whose surface area is selected by contact comprising:

a probe tip having an end surface that contacts said tissue surface area, a potential source for applying a group of sequential current pulses from said probe tip to each of successively selected tissue surface areas, the sequential pulses within each group occurring at a rate fast enough so that they are applied to substantially the same tissue surface area, a circuit for deriving values for a group of parameters indicative of the response to the group of sequential current pulses applied to each selected tissue surface area, a memory adapted to store a catalog of tissue types associated with respective subsets of groups of parameter values, and a processor for comparing the group of parameter values indicative of the response of a selected tissue surface area with the stored subsets of groups of parameter values to categorize said tissue surface area, wherein said probe tip further having optically coupled to it at least one light-emitting diode and a detector for detecting the light scattered back from the selected tissue surface area, the apparatus further comprising a circuit for measuring the bandgap potential of the light-emitting diode and adjusting accordingly the magnitude of the current pulses fed to the LED to compensate for temperature fluctuations.

16. An apparatus for categorizing biological tissue whose surface area is selected by contact comprising:

a probe tip having an end surface that contacts said tissue surface area, a potential source for applying a group of sequential current pulses from said probe tip to each of successively selected tissue surface areas, the sequential pulses within each group occurring at a rate fast enough so that they are applied to substantially the same tissue surface area, a circuit for deriving values for a group of parameters indicative of the response to the group of sequential current pulses applied to each selected tissue surface area, a memory adapted to store a catalog of tissue types associated with respective subsets of groups of parameter values, and a processor for comparing the group of parameter values indicative of the response of a selected tissue surface area with the stored subsets of groups of parameter values to categorize said tissue surface area, wherein said probe tip further having optically coupled to it at least one light-emitting diode, and a detector present at the probe tip for detecting the light scattered back from the selected tissue surface area, and wherein said detector receives light directly from said light-emitting diode and provides a signal proportional to the light output from said LED, and said apparatus further comprises an amplifier whose gain is changed in response to said signal to compensate for changes in the efficiency of said LED.

17. An apparatus for categorizing biological tissue whose surface area is selected by contact comprising:

a probe tip having an end surface that contacts said tissue surface area, a potential source for applying a group of sequential current pulses from said probe tip to each of successively selected tissue surface areas, the sequential pulses within each group occurring at a rate fast enough so that they are applied to substantially the same tissue surface area, a circuit for deriving values for a group of parameters indicative of the response to the group of sequential current pulses applied to each selected tissue surface area, a memory adapted to store a catalog of tissue types associated with respective subsets of groups of parameter values, and a processor for comparing the group of parameter values indicative of the response of a selected tissue surface area with the stored subsets of groups of parameter values to categorize said tissue surface area, wherein said probe tip further having optically coupled to it at least one light-emitting diode, and a detector present at the probe tip for detecting the light scattered back from the selected tissue surface area, and wherein said detector receives light directly from said light-emitting diode and provides a signal proportional to the light output from said LED, and said apparatus further comprises means to change the magnitude of a current pulse fed to said LED in response to said signal.

18. An apparatus for categorizing biological tissue whose surface area is selected by contact comprising:

a probe tip having an end surface that contacts said tissue surface area, a potential source for applying a group of sequential current pulses from said probe tip to each of successively selected tissue surface areas, the sequential pulses within each group occurring at a rate fast enough so that they are applied to substantially the same tissue surface area, a circuit for deriving values for a group of parameters indicative of the response to the group of sequential current pulses applied to each selected tissue surface area, a memory adapted to store a catalog of tissue types associated with respective subsets of groups of parameter values, and a processor for comparing the group of parameter values indicative of the response of a selected tissue surface area with the stored subsets of groups of parameter values to categorize said tissue surface area, wherein said parameter values are transformed as piecewise linear functions of a second parameter and associated with a degree of tissue abnormality, said transformed parameter comprising an integral of a portion of said parameter values for preselected time intervals and said second parameter comprises time.

19. An apparatus for categorizing biological tissue whose surface area is selected by contact comprising:

a probe tip having an end surface that contacts said tissue surface area, a potential source for applying a group of sequential current pulses from said probe tip to each of successively selected tissue surface areas, the sequential pulses within each group occurring at a rate fast enough so that they are applied to substantially the same tissue surface area, a circuit for deriving values for a group of parameters indicative of the response to the group of sequential current pulses applied to each selected tissue surface area, a memory adapted to store a catalog of tissue types associated with respective subsets of groups of parameter values, and a processor for comparing the group of parameter values indicative of the response of a selected tissue surface area with the stored subsets of groups of parameter values to categorize said tissue surface area, wherein said parameter values are transformed as piecewise linear functions of a second parameter and associated with a degree of tissue abnormality, said transformed parameter comprising the slope and intercept of the log voltage and said second parameter comprises inverse time.

20. An apparatus for categorizing biological tissue whose surface area is selected by contact comprising:

a probe tip having an end surface that contacts said tissue surface area, a potential source for applying a group of sequential current pulses from said probe tip to each of successively selected tissue surface areas, the sequential pulses within each group occurring at a rate fast enough so that they are applied to substantially the same tissue surface area, a circuit for deriving values for a group of parameters indicative of the response to the group of sequential current pulses applied to each selected tissue surface area, a memory adapted to store a catalog of tissue types associated with respective subsets of groups of parameter values, and a processor for comparing the group of parameter values indicative of the response of a selected tissue surface area with the stored subsets of groups of parameter values to categorize said tissue surface area, wherein said parameter values are transformed as piecewise linear functions of a second parameter and associated with a degree of tissue abnormality, said transformed parameter comprising the slope and intercept of the log voltage and said second parameter comprising log time.

21. An apparatus for categorizing biological tissue whose surface area is selected by contact comprising:

a probe tip having an end surface that contacts said tissue surface area, a potential source for applying a group of sequential current pulses from said probe tip to each of successively selected tissue surface areas, the sequential pulses within each group occurring at a rate fast enough so that they are applied to substantially the same tissue surface area, a circuit for deriving values for a group of parameters indicative of the response to the group of sequential current pulses applied to each selected tissue surface area, a memory adapted to store a catalog of tissue types associated with respective subsets of groups of parameter values, and a processor for comparing the group of parameter values indicative of the response of a selected tissue surface area with the stored subsets of groups of parameter values to categorize said tissue surface area, wherein said parameter values are transformed as piecewise linear functions of a second parameter and associated with a degree of tissue abnormality, said transformed parameter comprising arithmetic transformation of the parameter to diminish a predetermined obscuration effect of some artifact of, or noise source within the system and said second parameter comprising time.

22. An apparatus for categorizing biological tissue whose surface area is selected by contact comprising:

a probe tip having an end surface that contacts said tissue surface area, a potential source for applying a group of sequential current pulses from said probe tip to each of successively selected tissue surface areas, the sequential pulses within each group occurring at a rate fast enough so that they are applied to substantially the same tissue surface area, a circuit for deriving values for a group of parameters indicative of the response to the group of sequential current pulses applied to each selected tissue surface area, a memory adapted to store a catalog of tissue types associated with respective subsets of groups of parameter values, and a processor for comparing the group of parameter values indicative of the response of a selected tissue surface area with the stored subsets of groups of parameter values to categorize said tissue surface area, wherein said parameter values are transformed as piecewise linear functions of a second parameter and associated with a degree of tissue abnormality, said transformed parameter comprising voltage at the start of the relaxation curve and said second parameter comprising current.

23. An apparatus for categorizing biological tissue whose surface area is selected by contact comprising:

a probe tip having an end surface that contacts said tissue surface area, a potential source for applying a group of sequential current pulses from said probe tip to each of successively selected tissue surface areas, the sequential pulses within each group occurring at a rate fast enough so that they are applied to substantially the same tissue surface area, a circuit for deriving values for a group of parameters indicative of the response to the group of sequential current pulses applied to each selected tissue surface area, a memory adapted to store a catalog of tissue types associated with respective subsets of groups of parameter values, and a processor for comparing the group of parameter values indicative of the response of a selected tissue surface area with the stored subsets of groups of parameter values to categorize said tissue surface area, wherein said parameter values are transformed parameters of the inrush current as piecewise linear functions of parameters of a relaxation curve.

24. An apparatus for categorizing biological tissue whose surface area is selected by contact comprising:

a probe tip having an end surface that contacts said tissue surface area, a potential source for applying a group of sequential current pulses from said probe tip to each of successively selected tissue surface areas, the sequential pulses within each group occurring at a rate fast enough so that they are applied to substantially the same tissue surface area, a circuit for deriving values for a group of parameters indicative of the response to the group of sequential current pulses applied to each selected tissue surface area, a memory adapted to store a catalog of tissue types associated with respective subsets of groups of parameter values, and a processor for comparing the group of parameter values indicative of the response of a selected tissue surface area with the stored subsets of groups of parameter values to categorize said tissue surface area, wherein said parameter values are transformed as integrals of parameter values over voltage intervals and associated with a degree of tissue abnormality.

25. An apparatus for categorizing biological tissue whose surface area is selected by contact comprising:

a probe tip having an end surface that contacts said tissue surface area, a potential source for applying a group of sequential current pulses from said probe tip to each of successively selected tissue surface areas, the sequential pulses within each group occurring at a rate fast enough so that they are applied to substantially the same tissue surface area, a circuit for deriving values for a group of parameters indicative of the response to the group of sequential current pulses applied to each selected tissue surface area, a memory adapted to store a catalog of tissue types associated with respective subsets of groups of parameter values, and a processor for comparing the group of parameter values indicative of the response of a selected tissue surface area with the stored subsets of groups of parameter values to categorize said tissue surface area, wherein said parameter values are transformed as integrals of parameter values over current intervals and associated with a degree of tissue abnormality.

26. An apparatus for categorizing biological tissue whose surface area is selected by contact comprising:

a probe tip having an end surface that contacts said tissue surface area, a potential source for applying a group of sequential current pulses from said probe tip to each of successively selected tissue surface areas, the sequential pulses within each group occurring at a rate fast enough so that they are applied to substantially the same tissue surface area, a circuit for deriving values for a group of parameters indicative of the response to the group of sequential current pulses applied to each selected tissue surface area, a memory adapted to store a catalog of tissue types associated with respective subsets of groups of parameter values, and a processor for comparing the group of parameter values indicative of the response of a selected tissue surface area with the stored subsets of groups of parameter values to categorize said tissue surface area, wherein said parameter values are transformed as magnitudes of offsets of parameter values and associated with a degree of tissue abnormality.

27. An apparatus for categorizing biological tissue whose surface area is selected by contact comprising:

a probe tip having an end surface that contacts said tissue surface area, a potential source for applying a group of sequential current pulses from said probe tip to each of successively selected tissue surface areas, the sequential pulses within each group occurring at a rate fast enough so that they are applied to substantially the same tissue surface area, a circuit for deriving values for a group of parameters indicative of the response to the group of sequential current pulses applied to each selected tissue surface area, a memory adapted to store a catalog of tissue types associated with respective subsets of groups of parameter values, and a processor for comparing the group of parameter values indicative of the response of a selected tissue surface area with the stored subsets of groups of parameter values to categorize said tissue surface area, wherein, for any current pulse for which a tissue response is desired, multiple measurements of the tissue potential are taken during decay of the potential following application of the current pulse, wherein at least two parameter values are derived during the potential decay following each current pulse for which a tissue response is desired, and wherein said probe tip has at least two electrodes for applying current pulses to a selected tissue surface area and the polarity of said electrodes are reversed from time to time such that electrode degradation by electrochemical effects is reduced.

* * * * *